United States Patent
Martin

(12)
(10) Patent No.: US 6,316,180 B1
(45) Date of Patent: Nov. 13, 2001

(54) ELECTROCHEMILUMINESCENT MONITORING OF COMPOUNDS/ELECTROCHEMILUMINESCENCE ASSAYS

(75) Inventor: Mark T. Martin, N. Bethesda, MD (US)

(73) Assignee: IGEN International, Inc., Gaithersburg, MD (US)

( * ) Notice: Subject to any disclaimer, the term of this patent is extended or adjusted under 35 U.S.C. 154(b) by 0 days.

(21) Appl. No.: 08/880,353

(22) Filed: Jun. 23, 1997

Related U.S. Application Data

(63) Continuation-in-part of application No. 08/485,419, filed on Jun. 7, 1995, now Pat. No. 5,643,713, and a continuation-in-part of application No. 08/368,429, filed on Jan. 4, 1995, now Pat. No. 5,641,623.

(51) Int. Cl.[7] .............................. C12Q 1/00; C12Q 1/34; C12Q 1/02; G01N 33/53
(52) U.S. Cl. ............................ 435/4; 435/7.32; 435/7.1; 435/7.2; 435/18; 435/29; 435/34; 435/39; 424/1.69; 549/34
(58) Field of Search ........................... 435/4, 7.32, 7.1, 435/7.2, 7.72, 18, 29, 34, 39; 424/1.69; 549/34

(56) References Cited

U.S. PATENT DOCUMENTS

| | | | |
|---|---|---|---|
| 4,238,195 | 12/1980 | Boguslaski et al. | 435/4 |
| 4,372,745 | 2/1983 | Mandle et al. | 435/4 |
| 4,396,579 | 8/1983 | Schroeder et al. | 435/4 |
| 4,470,459 | 9/1984 | Copeland | 435/4 |
| 4,647,532 | 3/1987 | Wantanabe et al. | 435/4 |
| 4,994,377 | 2/1991 | Nakamura et al. | 435/4 |
| 5,093,238 | 3/1992 | Yamashoji et al. | 435/4 |
| 5,221,605 | 6/1993 | Bard et al. | 435/4 |
| 5,235,808 | 8/1993 | Taylor | 435/4 |
| 5,238,610 | 8/1993 | Thompson | 435/4 |
| 5,264,346 | 11/1993 | Chen | 435/4 |
| 5,310,687 | 5/1994 | Bard et al. | 435/4 |
| 5,641,623 | * 6/1997 | Martin | 435/4 |
| 5,643,713 | * 7/1997 | Liang et al. | 435/4 |

FOREIGN PATENT DOCUMENTS

WO84/03303  8/1984  (WO).

OTHER PUBLICATIONS

Vilim and Wilhelm "What Do We Measure By a Luminol–Dependent Chemiluminescence of Phagocytes?" 6, Free Radical Biology & Medicine, 623–629 (1989).

(List continued on next page.)

Primary Examiner—Louise N. Leary
(74) Attorney, Agent, or Firm—Whitman Breed Abbott & Morgan LLP

(57) ABSTRACT

Detectable compounds comprising a chemically-transformable first compound covalently linked to an electrochemiluminescent compound are provided. Such compounds are useful in processes and kits that monitor the status of the first compound and derive information from such monitoring.

A rapid single step assay suitable for the detection or quantification of β-lactam antibiotics and β-lactamases. The assay can be performed directly on samples of food, such as milk and meat, blood or serum and is useful in determining the suitability of a particular antibiotic in treating a particular bacterial infection and in diagnosis of a bacterial infection. The assay is also useful in determining and quantifying β-lactam antibiotic resistance. The assay can be performed on an IGEN Origen[R] Analyzer.

9 Claims, 25 Drawing Sheets

ECL REACTION WITH TRIPROPYLAMINE

OTHER PUBLICATIONS

Allain, C.C., et al "Enzymatic Determination of Total Serum Cholesterol," 20, Clinical Chemistry, 470–475 (1974).

Rubinstein and Bard, "Electrogenerated Chemiluminescence" 37.

Yang et al., "Electrochemiluminescence: A New Diagnostic and Research Tool", 12 Bio/Technology, 193–194 (Feb. 1994).

Massey, Biomedical Products, (Oct. 1992).

Blackburn et al., "Electrochemiluminescene Detection for Development of Immunoassays and DNA Probe Assays for Clinical Diagnostics", 37/9 Clin. Chem., 1534–1539 (1991).

Leland et al., 137 J. Electrochem. Soc., 3127–3131 (1990).

Payne D.J. "Metallo–β–lactamases: a new therapeutic challenge", 39 J. Med. Micro, 93–99 (1993).

Coulton & Francois, L., "β–Lactamases: Targets for Drug Design", 31 Prog. Med. Chem., 297–349 (1994).

Moellerir C., Jr., 31 J. Antimicrob, Chemother, (1993).

Neu, H.C., "The Crisis in Antibiotic Resistance" 257 Science, 1064–1072 (Aug. 11, 1992).

W.L. Baker, "Co–existence of β–lactamase and penicillin acylase in bacteria; detection and quantitative determination of enzyme activities" 73, No. 1, J. Appl. Bacteriol, 14–22 (1992).

A.C. Peterson et al., "Evaluation of Four Qualitative Methods for Detection of B–lactamase Production in Staphylococcus and Micrococcus Species" 8, No. 11 Eur. J. Clin. Microbiol. Infect. Dis., 962–967 (1989).

Robert H. Yolken et al., "Rapid Diagnosis of Infections Caused by β–lactamase–Producing Bacteria Producing Bacteria by Means of an Enzyme Radioisotopic Assay" 97,No. 5 The Journal of Pediatrics, 715–720 (Nov. 1980).

Therese M. Downey et al., "Chemiluminescence Detection Using Regenerable Tris(2,2'–bipyridyl)ruthenium(II) Immobilized in Nafion", Anal. Chem., 1992, 64, 261–268.

* cited by examiner

ECL REACTION WITH TRIPROPYLAMINE

PROPOSED ECL REACTION WITH β-LACTAMS

FIG. 7
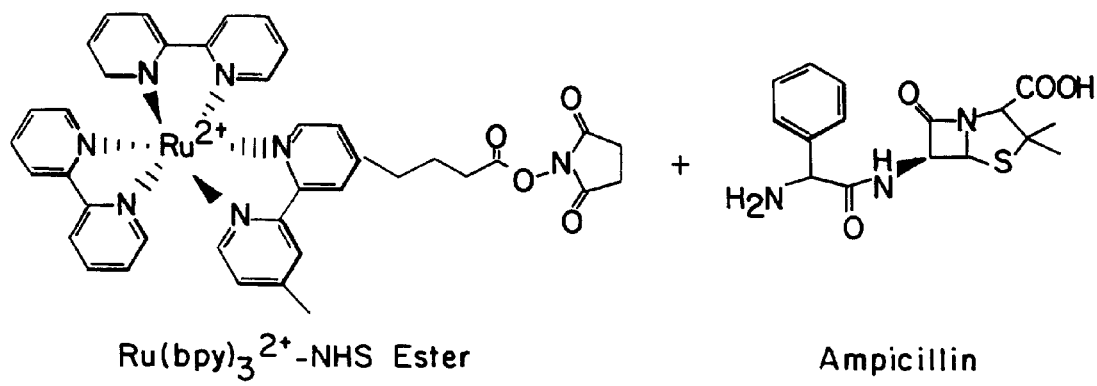
Ru(bpy)$_3^{2+}$-NHS Ester    +    Ampicillin
0.2 M Sodium Bicarbonate
2 Hours
Room Temperature
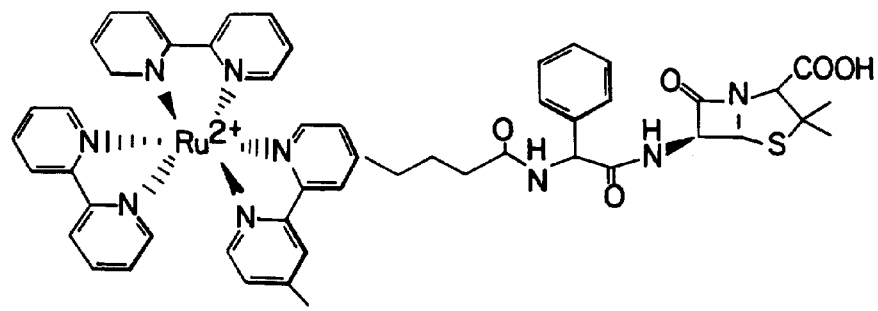
Ruthenium-Labelled Ampicillin (Ru-Amp)

β-LACTAMS

AMPICILLIN

AMOXICILLIN

PENICILLIN G

MOXALACTAM

CEFOXITIN

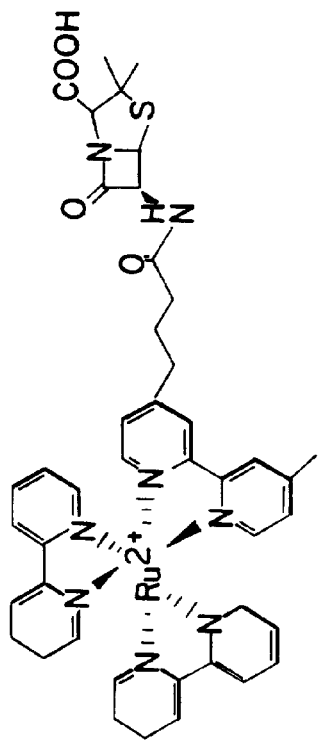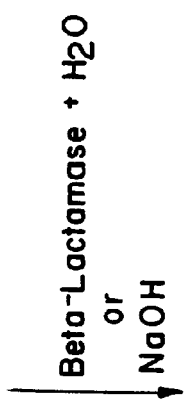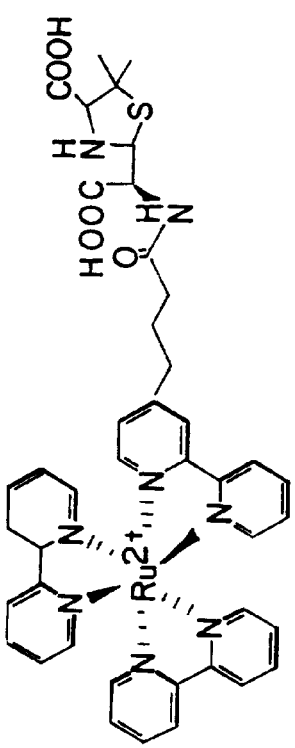
FIG 9B  Ruthenium-Labelled 6-Aminopenicillanic Acid (Ru-APA)
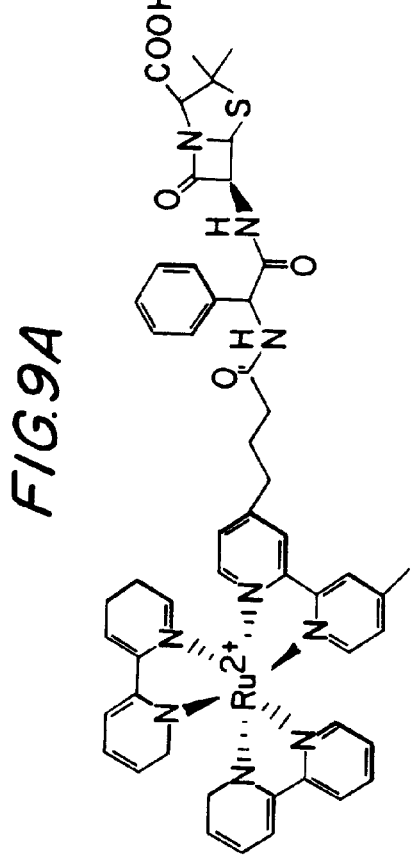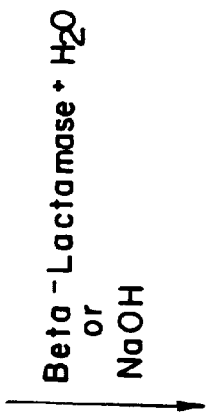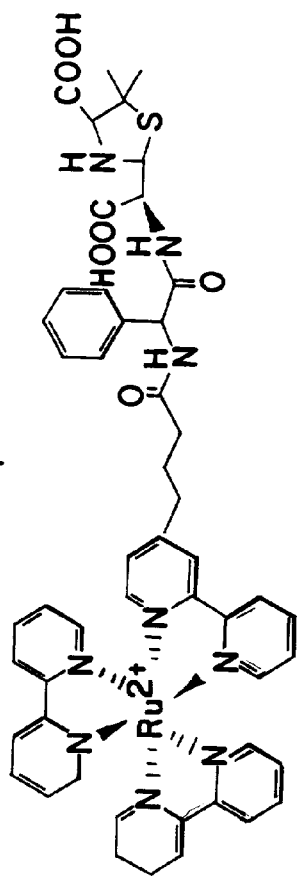
FIG 9A  Ruthenium-Labelled Ampicillin (Ru-Amp)

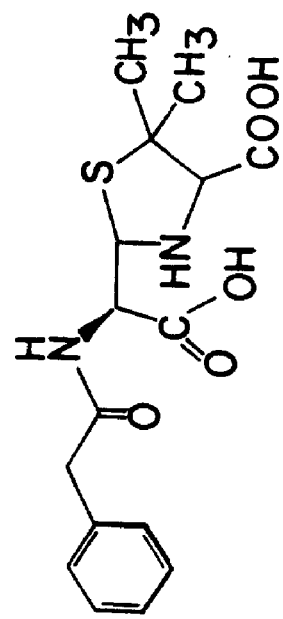
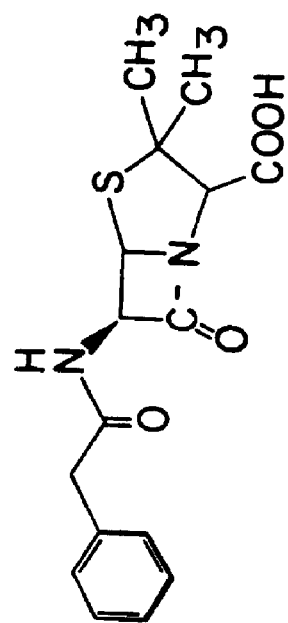
FIG.18

Amoxicillin

Ampicillin

Benzylpenicillin (Penicillin G)

Cefoxitin

Moxalactam

7-Aminocephalosporanic acid

6-Aminopenicillanic acid

Cefuroxime

Cephalosporin C

Cefaclor

ELECTROCHEMILUMINESCENT MONITORING OF COMPOUNDS/ ELECTROCHEMILUMINESCENCE ASSAYS

This application is a continuation in part of application Ser. No. 08/485,419, filed Jun. 7, 1995, now U.S. Pat. No. 5,643,713. This application is also a continuation in part of application Ser. No. 08/368,429, filed Jan. 4, 1995, now U.S. Pat. No. 5,641,623.

FIELD OF THE INVENTION

The present invention is directed generally to analytical biochemistry. More specifically, the present invention is useful for monitoring chemical transformations of detectable compounds having a chemically-transformable first compound covalently linked to an electrochemiluminescent compound.

The present invention also relates to the development of an electrochemiluminescence (ECL) based assay for the detection and the quantitative measurement of β-lactams and β-lactamases which assay is suitable for the diagnosis and the monitoring of the treatment of bacterial infections.

BACKGROUND OF THE INVENTION

An ever-expanding field of applications exists for rapid, highly specific, sensitive, and accurate methods of detecting and quantifying chemical, biochemical, and biological substances, including enzymes such as may be found in biological samples. Because the amount of a particular analyte of interest such as an enzyme in a typical biological sample is often quite small, analytical biochemists are engaged in ongoing efforts to improve assay performance characteristics such as sensitivity.

One approach to improving assay sensitivity has involved amplifying the signal produced by a detectable label associated with the analyte of interest. In this regard, luminescent labels are of interest. Such labels are known which can be made to luminesce through photoluminescent, chemiluminescent, or electrochemiluminescent techniques. "Photoluminescence" is the process whereby a material luminesces subsequent to the absorption by that material of light (alternatively termed electromagnetic radiation or emr). Fluorescence and phosphorescence are two different types of photoluminescence. "Chemiluminescent" processes entail the creation of the luminescent species by a chemical reaction. "Electrochemiluminescence" is the process whereby a species luminesces upon the exposure of that species to electrochemical energy in an appropriate surrounding chemical environment.

The signal in each of these three luminescent techniques is capable of very effective amplification (i.e., high gain) through the use of known instruments (e.g., a photomultiplier tube or pmt) which can respond on an individual photon by photon basis. However, the manner in which the luminescent species is generated differs greatly among and between photoluminescent, chemiluminescent, and electrochemiluminescent processes. Moreover, these mechanistic differences account for the substantial advantages as an bioanalytical tool that electrochemiluminescence [hereinafter, sometimes "ECL"] enjoys vis a vis photoluminescence and chemiluminescence. Some of the advantages possible with electrochemiluminescence include: (1) simpler, less expensive instrumentation; (2) stable, nonhazardous labels; and (3) increased assay performance characteristics such as lower detection limits, higher signal to noise ratios, and lower background levels.

As stated above, in the context of bioanalytical chemistry measurement techniques, electrochemiluminescence enjoys significant advantages over both photoluminescence and chemiluminescence. Moreover, certain applications of ECL have been developed and reported in the literature. U.S. Pat. Nos. 5,147, 806; 5,068,808; 5,061,445; 5,296,191; 5,247, 243; 5,221,605; 5,238,808, and 5,310,687, the disclosures of which are incorporated by reference, detail certain methods, apparatuses, chemical moieties, inventions, and associated advantages of ECL.

Copending and commonly-assigned U.S. patent application Ser. No. 08/368,429, filed January 4, 1995, the disclosure of which is incorporated by reference, details certain aspects of ECL in connection with beta-lactam and beta-lactamase (neither of which is conjugated through a covalent linkage to an electrochemiluminescent compound).

None of the above-identified documents disclose nor suggest the present invention. Additionally, the practice of the invention offers significant advantages to the skilled bioanalytical chemist in comparison to the electrochemiluminescent techniques taught by these documents. Accordingly, the invention meets the as-yet unmet needs of skilled workers with respect to the achievement of improved assay performance characteristics (e.g., signal output, detection limits, sensitivity, etc.) for the measured species and represents a patentable advance in the field.

Assays based on ECL are well known in the art and are finding expanding applications because of their accuracy, ease of use and freedom from radioactive materials.

A particularly useful ECL system is described in a paper by Yang et al, *Bio/Technology*, 12, pp. 193–194 (Feb. 1994). See also a paper by Massey, *Biomedical Products*, October 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al (1991) Clin. Chem. 37/9, pp. 1534–1539, the authors used the ECL reaction of ruthenium (II) tris (bipyridyl), $Ru(bpy)_3^{+2}$, with tripropylamine (TPA) (Leland et al (1990) J. Electrochem. Soc. 137:3127–31) to demonstrate the technique. Salts of $Ru(bpy)_3^{+2}$ are very stable, water-soluble compounds that can be chemically modified with reactive groups on one of the bipyridyl ligands to form activated species with which proteins, haptens, and nucleic acids are readily labeled. The activated form of the Ru(bpy) $_3^{+2}$ used by Blackburn et al was $Ru(bpy)_3^{+2}$-NHS ester:

Beta-lactamases which hydrolyze the amide bonds of the β-lactam ring of sensitive penicillins and cephalosporins are widely distributed amongst microorganisms and play a role in microbial resistance to P-lactam antibiotics. Beta-lactamases constitute a group of related enzymes which are elaborated by a large number of bacterial species but not by mammalian tissues and can vary in substrate specificities. See generally Payne, D.J., J. Med. Micro (1993) 39, pp. 93–99: Coulton, S. & Francois, L., Prog. Med. Chem. (1994) 31, 297–349; Moellering, R.C., Jr., J. Antimicrob. Chemother. (1993) 31 (Suppl. A), pp. 1–8: and Neu, H.C., Science (1992) 257, pp. 1064–1072.

The detection of β-lactamase activity in a body fluid has long been considered to be indicative of a recent or current bacterial infection.

The developing microbial resistance to antibiotics such as penicillin and cephalosporin has been of concern for awhile. Recently, this concern has escalated in light of the dwindling number of new antibiotics and the over-use of those which are known. It is becoming more imperative to select the optimum antibiotic for treating a particular infection and to avoid prescribing the latest antibiotic when effective alternatives exist. This ability to select the optimum antibiotic is especially critical in those facilities involved in long-term care facilities where antibiotic resistance is increasingly becoming a problem. The lifetime of the current family of antibiotics can be prolonged by the selection of the optimum antibiotic. See generally Harold C. Neu, "The Crisis in Antibiotic Resistance", *Science* Vol. 257 (Aug. 11, 1992) pp. 1064–1072.

The rising resistance to microbial resistance to antibiotics has heightened the need for a test which can rapidly measure quantitatively the degree of resistance to a particular β-lactam antibiotic such as a penicillin or a cephalosporin and then select the most appropriate antibiotic for a particular infective condition.

Several methods currently exist for the detection of microbial β-lactamases. Some representative examples follow.

W.L. Baker, "Co-existence of β-lactamase and penicillin acylase in bacteria: detection and quantitative determination of enzyme activities", *J. Appl. Bacteriol.* (1992) Vol. 73, No. 1, pp. 14–22 discloses a copper-reducing assay for the detection of penicilloates and a fluorescamine assay to detect 6-aminopenicillanic acid concentrations when both substances were produced by the action of the enzymes on a single substrate.

U.S. Pat. No. 5,264,346 discloses a calorimetric assay for β-lactamase which has a variety of applications. The assay is based on the decolorization of a chromophore formed by oxidation of either the N-alkyl derivative of p-phenylenediamine or the 3,3',5,5'-tetraalkyl derivative of benzidine. The decolorization is attributed to the presence of an open β-lactam ring product resulting from the hydrolysis of cephalosporin or penicillin. Decolorization with the open β-lactam product of penicillin requires the presence of a decolorization enhancer such as mercury containing compounds. The enhancer is not required for decolorization with the open β-lactam product of cephalosporin.

U.S. Pat. No. 4,470,459 discloses a rapid method for the detection of the presence of β-lactamase from microbial sources which is based on a β-lactamase conversion of a β-lactam substrate which reverses its ability to fluoresce. Specific β-lactams mentioned as having this property include ampicillin, cephalexin, amoxicillin, cefadroxil and cephaloglycin. The change in the ability to fluoresce is attributed to the presence of β-lactamase.

WO 84/03303 discloses a microbiological test process for identifying producers of β-lactamase. The assay relies on changes in acidity which affect the fluorescence of the indicator such as coumarin. This change in acidity is attributed to the conversion product produced by the presence of the β-lactamase.

A.C. Peterson et al, "Evaluation of four qualitative methods for detection of β-lactamase production in Staphylococcus and Micrococcus species", *Eur. J. Clin. Microbiol. Infect. Dis.* (1989), Vol. 8, No. 11, pp. 962–7 presents certain factors which were employed in evaluating qualitative assays for β-lactamase.

Robert H. Yolken et al, "Rapid diagnosis of infections caused by β-lactamase-producing bacteria by means of an enzyme radioisotopic assay", *The Journal of Pediatrics*, Vol. 97, No. 5 (Nov. 1980) pp. 715–720 discloses a sensitive enzymatic radioisotopic assay for the measurement of β-lactamase as a rapid test for detection of bacterial infection. The assay protocol involves an incubation step with sample followed by the separation step on a positively charged column such as DEAE-Sephacel prior to measurement of the radioactivity of eluted fractions. The β-lactamase converted penicillinic product has an additional carboxyl group which insures its stronger binding to the positively charged column than the penicillin. Differences in radioactivity between the eluted fractions and the original values are attributed to the presence of β-lactamase.

Prior to the invention disclosed herein, there remains a need for a universal assay for β-lactams and β-lactamases which is both very rapid (10 minutes or less) and also very sensitive.

The invention disclosed within this application achieves these needs by adapting electrochemiluminescence methodologies to the measurement of β-lactams or β-lactamases. Other objects of the invention will also be apparent from the description of the invention which follows.

SUMMARY OF THE INVENTION

The present invention is directed to compounds, processes, and kits useful for electrochemiluminescent monitoring of compounds. A critical feature of the invention which is common to these compounds, processes, and kits is detectable compounds comprising a chemically-transformable first compound covalently linked to an electrochemiluminescent compound.

In brief, these detectable compounds and their uses represent a patentable advance in the field of electrochemiluminescent measurements because of their attributes. These attributes include the following:

1. They are electrochemiluminescent.;
2. They can be used to monitor chemically-transformable first compounds covalently linked to electrochemiluminescent compounds.; and
3. The above-described monitoring can be extended to become an integral step in performing assays for separate, nonconjugated compounds in sample solutions (e.g., enzymes).

Applicants' present inventions are set forth immediately below in the following nonexclusive, nonlimiting objects of the invention.

A first object of the invention is to provide electrochemiluminescent detectable compounds comprising a chemically-transformable first compound covalently linked to an electrochemiluminescent compound.

A second object of the invention is to provide electrochemiluminescent processes for monitoring chemical transformations of the first compound. Consistent with this second object, assays are provided wherein the chemical transformation of the first compound is an integral step in performing that assay.

A third object of the invention is to provide kits useful for practicing the invention and for-implementing the above-described first and second objects of the invention. Consistent with is this third object, kits are provided wherein at least one set of solutions containing the detectable 16 compounds is included.

Broadly stated, the invention also contemplates an electrochemiluminesence based assay for the detection of β-lactamases or β-lactam moieties. The invention has as one of its objects an universal assay for β-lactam antibiotics as well as β-lactamases which are both rapid (10 minutes or less) and sensitive (low micromolar concentrations of antibiotics and picomolar concentrations of β-lactamases). The assay would be suitable for the detection as well as the quantification of the β-lactam antibiotics and β-lactamases.

Central to use of electrochemiluminesence methodology as a measuring system for β-lactamases and β-lactams was the recognition by applicants that β-lactam antibiotics and/or their hydrolysis products will cause Ru(bpy)$_3^{+2}$ to emit light in the ECL instrument. Moreover, with all β-lactams tested, there is a substantial difference between intact antibiotics and their hydrolysis products in this ability. Accordingly, a change in chemiluminescence correlates with the presence of β-lactamase activity.

Equally surprising to applicants was the versatility of the assay to the measurement of various β-lactam structures and thereby the β-lactamase family of enzymes. Critical to this is the conversion of the tertiary amine structure of the intact antibiotic structure to the structure of the secondary amine in the hydrolyzed product. The hydrolyzed and/or unhydrolyzed compound functions as tripropyl amine in the prior art chemiluminescent assays.

All that is required is to incubate the sample with β-lactam antibiotic of interest and to measure the change in chemiluminescence over time using established protocols and apparatus. What was also not expected by applicants at the time was the quality of the results achievable in a relatively short time (5 minutes to 2 hours) and the sensitivity achieved for both the β-lactam and β-lactamases. As evidenced in Table I on p. 264 by Downey et al., "Chemiluminescence Detection Using Regenerable Tris (2, 2'bypyridyl) ruthenium (II) Immobilized in Nafionp", Anal. Chem. 64 (1992) pp. 261–268, there was no appreciation prior to this invention that the hydrolized structure of penicillin produced appreciable amounts of ECL.

BRIEF DESCRIPTION OF THE DRAWINGS

FIG. 7 shows the synthesis of Ru-APA.

FIG. 9 shows the hydrolysis by NaOH or by beta-lactamase enzyme of Ru-AMP (left side) and of Ru-APA (right side).

FIG. 18 illustrates β-lactamase-catalyzed hydrolysis of benzylpenicillin.

FIG. 20 shows the quantitation of antibiotic hydrolysis using spectrophotometric (black bars) and ECL (gray bars) assay methods. As detailed in the text, the spectrophotometric methods varied depending on factors relating to unique characteristics of the electronic absorbance spectra of the unhydrolyzed and unhydrolyzed antibiotics, while a single ECL instrument method was used for all antibiotics. In all cases, 1.0 mM of each antibiotic was incubated at room temperature for 10 minutes with one of four enzymes.

DETAILED DESCRIPTION OF THE INVENTION

I. ELECTROCHEMILUMINESCENT MONITORING OF COMPOUNDS

The present invention is concerned with detectable compounds comprising (A) a chemically-transformable first compound (B) covalently linked to (C) an electrochemiluminescent compound. The salient features of each of these three portions [(A), (B), and (C)] of the detectable compounds are individually described below. Uses of the detectable compounds appear at (D) while specific examples of the present invention appear at (E).

(A) The chemically-transformble first compounds

The terms "chemically-transformable first compound(s)" (hereinafter "CTFC") and "electrochemiluminescent compound(s)" (hereinafter "EC") each refer to the respective compound independent of certain minor variations of that compound. The skilled worker will understand which minor variation, if any, applies to any particular usage of either CTFC or EC to by its context. The following explanations aid in the understanding of this context. The term CTFC encompasses the following minor variations: (i) certain changes in the formal redox state caused by reduction or oxidation reactions and certain chemical changes to the CTFC that do not destroy the covalent linkage between it and the EC (e.g., the ejection by the CTFC of $H^{+1}$); and (ii) certain chemical transformations (e.g., the hydrolysis of the CTFC) which alter the measurable luminescence of the detectable compound in comparison to the measurable luminescence before any of such chemical transformations have occurred.

In comparing the measurable luminescence of the detectable compound before and after such chemical transformation, several combinations are possible as detailed in the chart below.

| measurable luminescence before | measurable luminescence after | |
|---|---|---|
| none | yes (an increase from zero) | |
| yes | none (a decrease to zero) | |
| yes | yes (an increase from nonzero) | |
| yes | yes (a decrease from nonzero) | |
| yes | yes (no change) | INOPERATIVE |
| none | none | INOPERATIVE |

As depicted in this chart, the measurable luminescence of the detectable compound is altered by the chemical transformation of the CTFC; i.e., the measured luminescence before and after the chemical transformation differ from one another. However, there must be some measurable luminescence either before or after, or both before and after, any such chemical transformation. Thus, the fifth and sixth entries in the above chart do not represent compounds encompassed by the present invention while the first four entries do represent compounds encompassed by the present invention.

FIGS. 3(a–c) shows a proposed ECL mechanism depicting reaction steps associated with the use of a CTFC as a conjugated reductant that is covalently linked to an EC. More particularly, the EC is exemplified by the ruthenium (II) tris-bipyridyl cation (hereinafter "$Ru(bpy)_3^{+2}$") throughout FIGS. 3(a–c). FIGS. 3(a–c) illustrates contemplated minor variations in these two compounds (i.e., in a CTFC and in an EC).

Figure 3C:
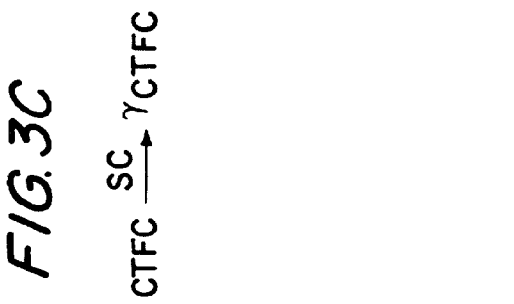
FIGS. 3(a–c) shows a proposed ECL mechanism depicting reaction steps associated with the use of a chemically-transformable first compound as a conjugated reductant.
Figure 3B:
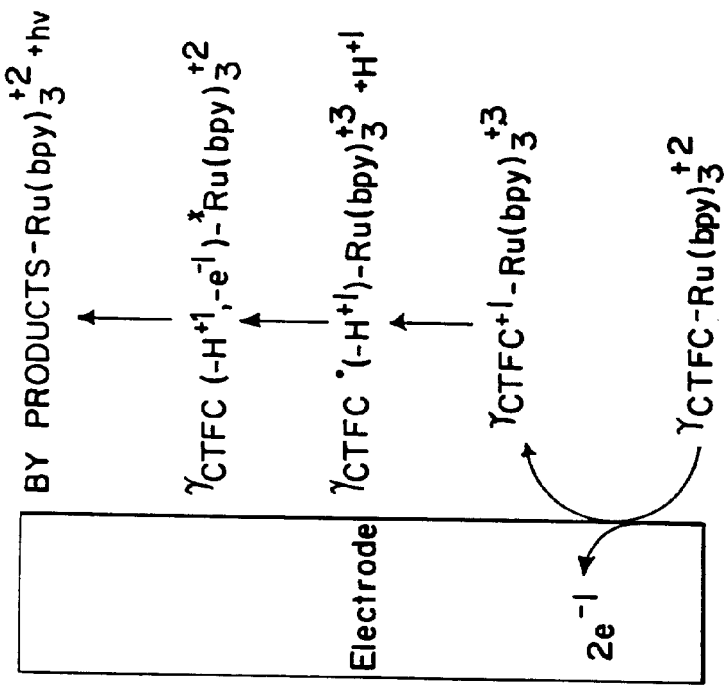
Figure 3A:
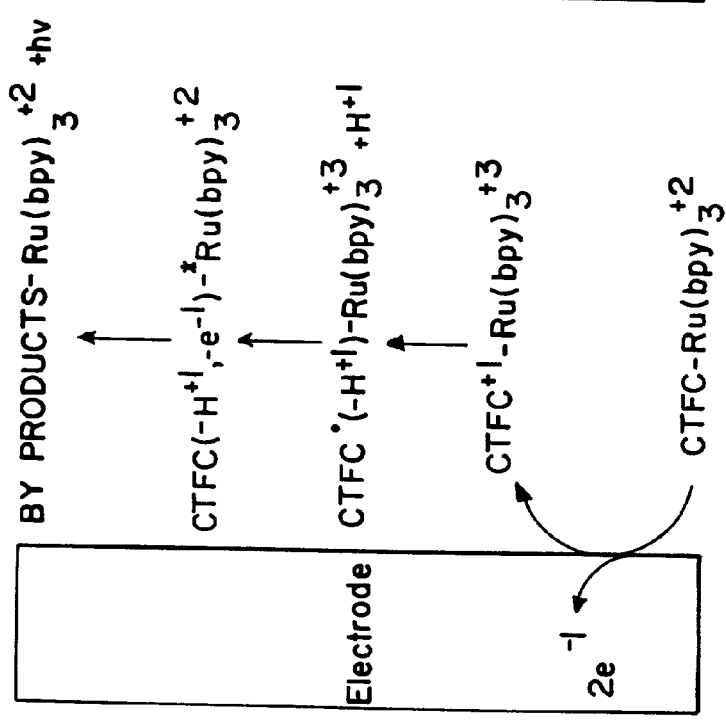

FIG. 3(a) depicts the postulated ECL mechanism for a detectable compound comprising a CTFC covalently linked to an EC. The chart below further explains the depicted reactions.

| Symbol | Definition |
|---|---|
| CTFC | electrochemically unchanged CTFC (starting compound) |

-continued

| Symbol | Definition |
|---|---|
| $CTFC^{*+1}$ | radical, electrochemically oxidized CTFC |
| $CTFC^*(—H^{+1})$ | radical, electrochemically neutral CTFC formed by $H^{+1}$ leaving $CTFC^{+1}$ and able to act as a high-energy reductant in a manner similar to TPA |
| $CTFC(—H^{+1}, —e^{-1})$ | electrochemically neutral, nonradical CTFC formed by $CTFC^*(—H^{+1})$ intramolecularly donating an electron ($e^{-1}$) to the covalently linked EC |
| $Ru(bpy)_3^{+2}$ | nonexcited EC before electrochemical oxidation |
| $Ru(bpy)_3^{+3}$ | nonexcited EC after electrochemical oxidation |
| $*Ru(bpy)_3^{+2}$ | excited EC after being intramolecularly reduced by the $CTFC^*(—H^{+1})$ |
| $Ru(bpy)_3^{+2}$ | nonexcited, regenerated EC formed by the emission of light by excited EC |
| hv | light emitted by the excited EC |

FIG. 3(b) shows, relative to FIG. 3(a), all of the analogous reactions to those of FIG. 3(a) with the exception that the symbol $^YCTFC$ is consistently used to represent the resulting chemically-transformed $^YCTFC$ that is produced by the interaction between a CTFC and a second compound (hereinafter "SC").

FIG. 3(c) shows the schematic depiction of the interaction between a CTFC with a SC to form the resulting $^YCTFC$.

The detectable compound depicted at FIGS. 3 (a), (b), (c) represents a compound of the present invention that is able to produce measurable luminescence both before and after the chemical transformation of the CTFC. Thus, this compound exemplifies the third and fourth possible combinations of measurable luminescence contained in the previously discussed chart. The depicted reactions are consistent with postulated reaction mechanisms which culminate in measurable luminescence both before and after the CTFC has been chemically transformed. For compounds of the present invention falling within the first and second entries of the previously discussed chart (i.e., for those compound that only produce measurable luminescence either before or (exclusively) after the chemical transformation of the CTFC), only the reaction mechanisms of either FIG. 3 (a) or (exclusively) FIG. 3 (b) is representative for any particular compound.

With regard to the minor variations of (i), both electrochemical redox reactions and non-electrochemical redox reactions are encompassed. Additionally, such changes are integral with and associated with the postulated electrochemiluminescent mechanism including (a) steps leading to the formation of a high-energy reductant as a form of the CTFC; and (b) steps leading to the actual luminescence by the EC.

With regard to the minor variations of (ii), chemical transformations that affect the intramolecular electron-donating ability of the CTFC when it acts as a high-energy reductant in electrochemiluminescence mechanisms are encompassed. The hydrolysis of a CTFC/substrate by either NaOH or an enzyme is an example of such a chemical transformation.

A critical feature of the CTFC is that it remains covalently linked to the EC throughout all of the postulated reactions. Thus, it is understood that the previously discussed changes in and to the CTFC specifically exclude changes which would destroy/break the covalently linkage of the CTFC to the EC. It is also understood that the changes in and to the CTFC alter the intramolecular electron-donating ability of the CTFC so that the measurable luminescence differs before and after any such changes. The CTFC is chosen so that there is measurable luminescence either before or (exclusively) after, or both before and after, any such changes.

Returning to the explanation of the term CTFC and the minor variations encompassed therein, the scope of these variations is clear to the skilled worker.

Figure 1:
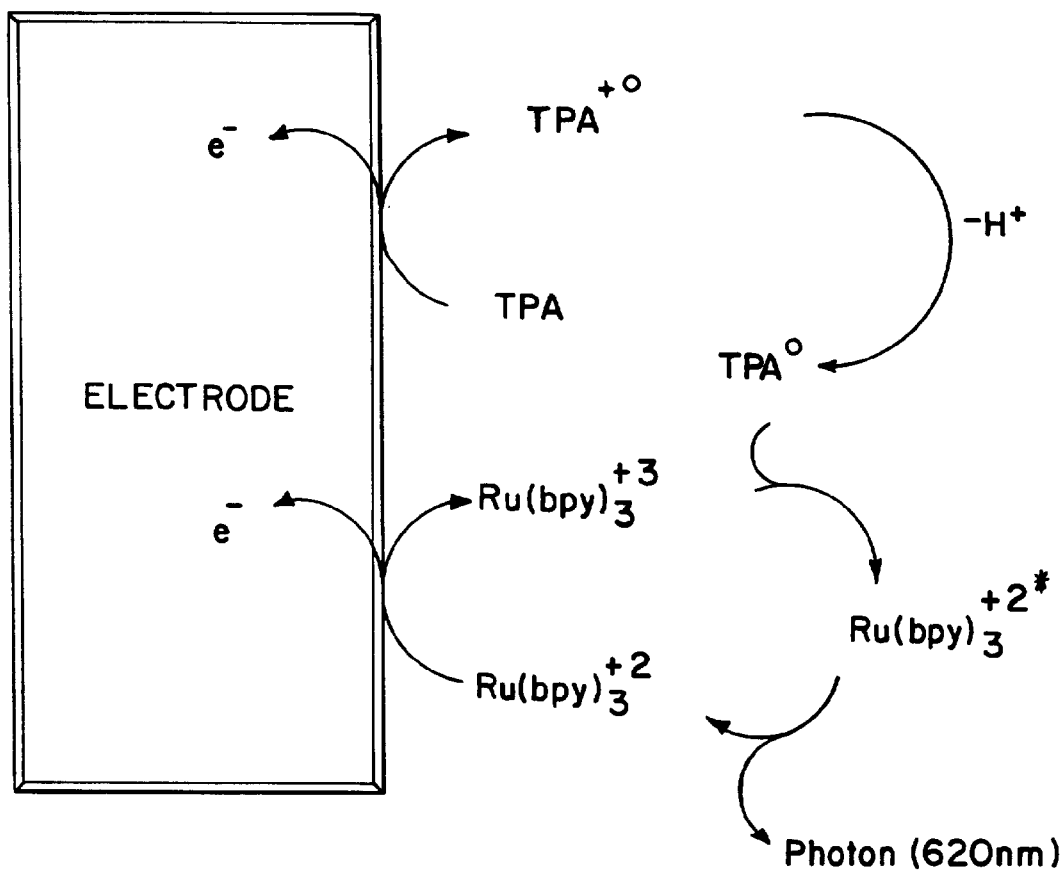
FIG. 1 shows a proposed ECL mechanism depicting reaction steps associated with the use of TPA as a nonconjugated reductant.

The CTFC must be able to participate in the ECL mechanisms that cause the EC to luminesce. Specifically, the CTFC must finction as a high-energy reductant capable of intramolecularly providing an electron to the EC so the EC is reduced into an excited (i.e., emissive) state. Suitable high-energy reductants for forming the excited state EC often have an unpaired electron and are knows as radicals. FIG. 1 illustrates a proposed ECL mechanisms which uses TPA as a nonconjugated high-energy reductant. This mechanisms generates the actual high-energy reductant in situ subsequent to the initial electrochemical oxidation (triggering) of the TPA precursor. Suitable candidates for the CTFC of the present invention are within the knowledge of the skilled worker based on the disclosure herein.

Applicants are not required to understand the theoretical underpinnings which explain the observed behavior of the detectable compounds. While not wishing to be bound by any particular scientific explanation for these observed properties, applicants postulate the following explanations (I) and (II).

(I.) The ability of the covalently linked CTFC to act as a high-energy reductant by intramolecularly donating an electron to the EC varies according to whether that CTFC has or has not yet undergone a suitable chemical transformation. This variance can, depending upon the particular CTFC involved, either increase or decrease the measured luminescence in any one of the four previously discussed combinations. The chemical transformation in a CTFC resulting from the interaction with a SC appears to cause this variance in intramolecular electron-donating ability because of structural changes in the CTFC which might effect (i) the route through which the reducing electron has to pass through; (ii) the ability of the reducing electron to begin traveling through any such route; or (iii) stereochemical/spatial orientation considerations.

(II.) The ability of the covalently linked CTFC to act as a high-energy reductant by intramolecularly donating an electron to the EC is greater in comparison to the ability of that same (nonconjugated) CTFC to intermolecularly donate an electron to the EC. Correspondingly, the measured luminescence for the detectable compounds of the present invention is greater in comparison with the measured luminescence of electrochemiluminescent compounds where the high energy reductant is not covalently linked to the electrochemiluminescent compound.

Figure 2:
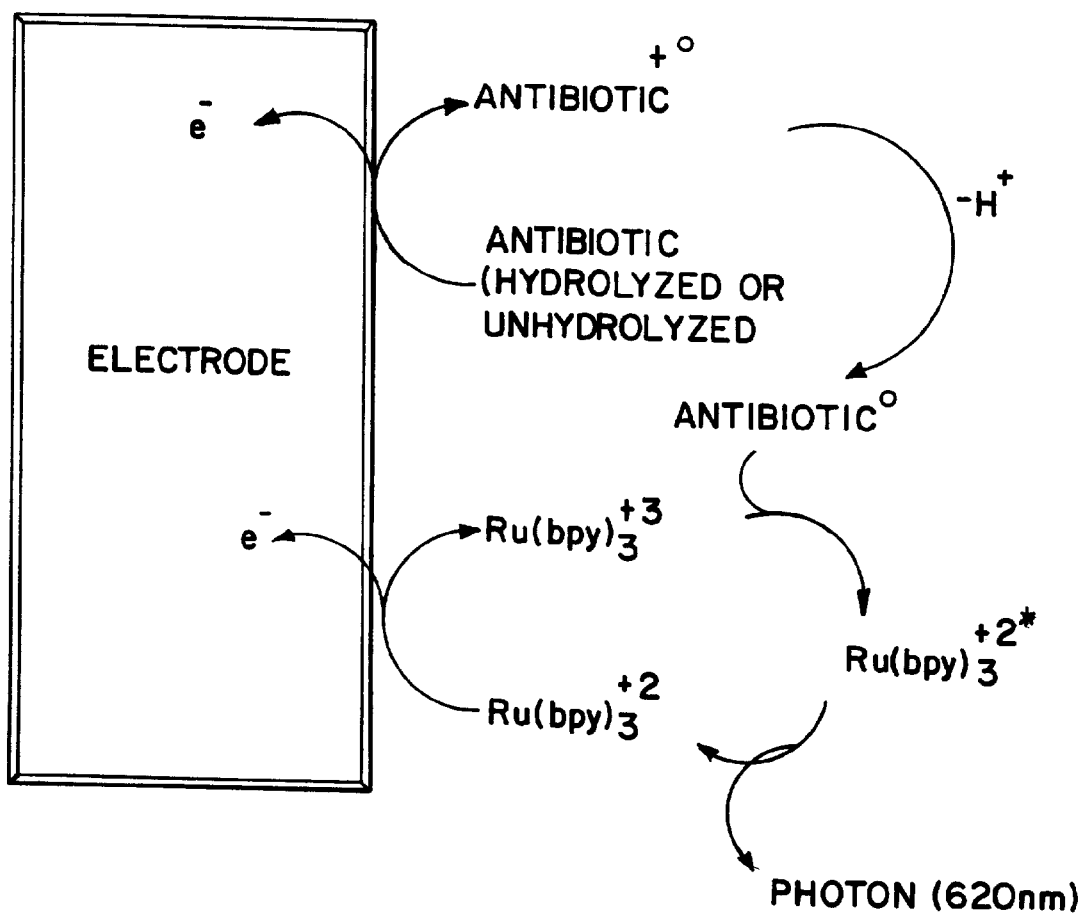
FIG. 2 shows a proposed ECL mechanism depicting reaction steps associated with the use of beta-lactam as a nonconjugated reductant.

Although nonconjugated high energy reductants are not the subject of the present invention; they nicely illustrate the importance of the mechanistic differences. Certain electrochemiluminescent techniques, however, have focused on using such nonconjugated high energy reductants. FIGS. 1 and 2 illustrate proposed electrochemiluminescent mechanisms with such nonconjugated reductants. Specifically, FIG. 1 depicts electrochemiluminescent reactions which use tri-n-propylamine (hereinafter "TPA" as such a reductant while FIG. 2 likewise depicts these reactions with beta-lactam as the reductant. The postulated electrochemiluminescence mechanism shown in FIG. 1 using nonconjugated TPA and $Ru(bpy)_3^{+2}$ has been previously reported in the literature. The postulated electrochemiluminescence mechanisms for beta-lactams (nonconjugated) shown in FIG. 2 [as noted previously, the use of beta-lactams as nonconjugated, high energy reductants in electrochemiluminescence techniques is the subject of a copending and commonly-assigned U.S. patent application] and for the conjugated high energy reductants of the present invention are derived in part from and are thought to be consistent with the mechanistic explanation for the TPA-induced electrochemiluminescence shown in FIG. 1.

Applicants theorize the following explanation as to why, for example, beta-lactam as a nonconjugated reductant generates less electrochemiluminescence than beta-lactam as conjugated reductant (i.e., as a CTFC). The nonconjugated beta-lactam must first diffuse through solution to become sufficiently proximate to the EC and then intermolecular donate an electron thereto. Moreover, during this diffusion process, the nonconjugated beta-lactam may react with any available species (other than the EC) because it is a very reactive, radical species. In direct contrast, the CTFC does not have to diffuse through the solution as a free species. The CTFC need only intramolecularly donate an electron to the covalently linked EC.

The above analysis teaches attributes of the CTFC sufficiently detailed to enable the skilled worker to practice the present invention. To augment the above teachings, applicants later provide examples using particularly-identified compounds as the CTFC. However, applicants' invention is not limited to any specific compounds; rather applicants' invention is limited only to suitable CTFC as taught by the foregoing.

(B) Tbe covalent linkage

The covalent linkage comprises a linker group that covalently links one of the chelating ligands of the EC to the CTFC. Thus, the near end of the linker group terminates with and extends into a covalent bond between an atom of the linker group and an atom of one of the chelating ligands of the EC while the far end of the linker group terminates with and extends into a covalent bond between an atom of the linker group and an atom of the CTFC.

This linker group must have the following attributes to ensure that applicants' detectable compounds are operative. As detailed below, these attributes are divided into two main categories; namely, noninterfering and enhancing.

The noninterfering attributes are properties that the linker group must have because otherwise their presence would interfere with the operability of the invention. Specifically, the linking group during the contemplated practice of the invention must not: (i) prohibit the electrochemical reactions; (ii) prohibit the interactions between the CTFC and the SC; (iii) prohibit the overall electrochemiluminescence mechanism; and (iv) be itself destroyed by the necessary reactions of the invention. For example, a linker group containing an electrochemically oxidizable species having a formal oxidation potential close to that of the central metal cation of the EC would not serve as an effective linking group.

The enhancing attributes of the linker group are those attributes that specifically relate to the ability of the CTFC to intramolecularly transfer an electron to the central metal cation of the EC. These enhancing attributes include the length of the linking group and the nature of the bonds within such length. First, the length of the intervening linker group between the CTFC and the EC must (i) allow and permit the appropriate intramolecular electron transfer to occur; and (ii) not prevent any necessary reaction from occurring due to steric or other considerations.

The term "intramolecular" transfer of an electron from the CTFC to the EC encompasses both transfer though bonds and through space. Such "intramolecular" transfers, however, limited to transfers between a donating compound (i.e., the CTFC) and a corresponding receiving compound (i.e., the EC) which are covalently linked to each other through the linking group. The covalent linkage portion of the detectable compounds must allow and permit at least one these two types of intramolecular transfer.

For intramolecular transfer through bonds, the linker group must provide sufficient delocalized, conductive electrons (e.g., conjugated π-systems) to enable the electron to travel through the bonds of the linking group to than reach the central metal cation of the EC.

For intramolecular transfer through space, the linker group must enable the CTFC to approach in relative close proximity the central metal cation of the EC. The linker group should be long enough and stereochemically flexible enough so that the CTFC attached to the far end of the linker group can swing back towards the metal cation and then the electron can intramolecularly transfer through the space then separating the CTFC and the EC. An additional limitation on the appropriate length of the linker group is that it should not be so long that the frequency of the described swinging around effect (which effect is thought to be necessary for intramolecular transfer through space) significantly decreases. In the case of an excessively long linker group, the amount of luminescence produced would be lowered.

For example, a linking group that is not sufficiently long/flexible to enable intramolecular transfer through space and contains only saturated bonds without any delocalized electrons (e.g., alkyl chains) would not be an effective linker group.

There are several advantages that the linker group imparts to the detectable compounds as compared to the electrochemiluminescent compounds that are used with nonconjugated high-energy reductants. The detectable compounds of the present invention avoid the use of any diffusion of free species through solutions. Possible advantages include a more rapid generation of the exited, luminescent-form of the EC and higher signals associated with the more effective intramolecular transfer of applicants' present invention as compared to the intermolecular transfer used with nonconjugated high-energy reductants.

This linkage also ensures that the ratio of the CTFC and the EC is one-to-one. This ratio is unlike that associated with electrochemiluminescent techniques which use TPA nonconjugated beta-lactams as the high-energy reductant. Because of this ratio between the two portion of the detectable compounds of the present invention, applicants are able to qualitatively and quantitatively monitor chemical transformations in the CTFC. Unlike known electrochemiluminescent techniques, the compound monitored is simultaneously (i) covalently linked to the EC and (ii) capable of intramolecularly donating an electron to the EC.

Suitable candidates to be tested as linker groups in the present invention are available to those of ordinary skill in the art. In particular, Vol. 136, Methods in Enzymology, K. Mosbach, Ed., pp. 3–30, Academic Press, NY (1987) discloses a series of "spacer molecules" for immobilized active coenzymes, including NAD and ATP. The spacer molecules of this article, which article is fully incorporated by reference, are examples of such suitable candidates. The above analysis, in connection with the disclosure herein, teaches attributes of the covalent linkage sufficiently detailed to enable the skilled worker to practice the present invention. Thus, the skilled worker can select appropriate candidates as linking groups and determine, by routine experimentation, those which do and do not work To augment the above teachings, applicants later provide examples using specific detectable compounds having identified linker groups. However, applicants' invention is not limited to any such exemplified linker group. Rather, the present invention is limited only to covalent linkages as taught herein to the skilled worker.

(C) The electrochemilumibesent compounds.

The third and final portion of the detectable compounds are EC. These and their applications in certain contexts have been reported in the literature. See, for example, the issued U.S. patents previously incorporated by reference. The attributes and identities of such known EC are known to skilled workers and need not be repeated in detail here. Thus, the term electrochemiluminescent compound is a term of art whose metes and bounds are known to skilled workers. Nonlimiting, nonexclusive examples of particular detectable compounds (including the EC portion) and their uses are later provided.

The present invention, however, is not directed to EC in and of themselves nor is it directed to any of their known applications. The invention is directed to a novel and nonobvious use of EC; namely, their use in detectable compounds comprising a CTFC covalently linked to an EC. Accordingly, the skilled worker can practice the present invention in accordance with the disclosure herein in combination with the existing knowledge of EC. Notwithstanding this, applicants provide guidelines for providing EC operative in the present invention.

The minor variations encompassed by the term CTFC discussed earlier at (A) apply in an analogous manner to those for the term EC and need not be reexamined here. Thus, changes in formal redox state of the EC due to, for example, electrochemical oxidation and intramolecular reduction as well as excited/nonexcited states are encompassed by the term EC and such changes represent acceptably differing forms of the EC.

The following formula (L) depicts suitable electrochemiluminescent compounds for use in the present invention:

$$M(L^1)_a(L^2)_b(L^3)_c(L^4)_d(L^5)_e(L^6)_f \qquad (I.)$$

wherein

M is a central metal cation comprising ruthenium or osmium;

$L^1$ through $L^6$ are each ligands of M, each of which may be monodentate or polydentate, and each of which may be the same or different from each other;

a through e are each 0 or 1;

provided that the ligands of M are of such number and composition that the compound can be induced to electrochemiluminescence; and further provided that the total number of bonds provided by the ligands to the central metal cation M equals the coordination number of M.

In the practice of the present invention, preferred electrochemiluminescent compounds include those wherein the central metal cation is ruthenium Ru or osmium Os. A particularly preferred compound is $Ru(bpy)_3^{+2}$.

Having established (i) that electrochemiluminescent compound is a term of art; (ii) guidelines for providing such EC; the term EC as used herein is clear to skilled workers. Nonetheless, applicants later amplify this teaching by providing nonlimiting, nonexclusive particular examples which identify the EC.

(D) Uses of the detectable compounds.

The identities, attributes, and theoretical basis of the detectable compounds of the present invention have previously been detailed. Consequently, this section details the uses of such detectable compounds.

The electrochemiluminescent processes that use the detectable compounds can be viewed as being divided into two main categories; namely, monitoring and assaying.

The detectable compounds can be used to monitor chemical transformations in the CTFC that alter the effective intramolecular donating ability of that CTFC. These monitoring processes are not primarily designed to qualitatively nor quantitatively identify the presence/amount of any particular SC. Rather, the monitoring processes are designed to qualitatively and/or quantitatively indicate the presence/extent of chemical transformations in the CTFC without requiring identifications directed to which particular SC in the sample solution is responsible for any such chemical transformations.

By comparing (i) the measured luminescence of the detectable compound after the exposure of that detectable compound to sample solutions suspected of containing at least one SC that is capable of interacting with the CTFC and of effecting a chemical transformation in the CTFC with (ii) the measured luminescence of the predetermined standard, the CTFC is effectively monitored. More specifically, the presence and extent of such chemical transformations in the CTFC can be monitored. The predetermined luminescence standard of the monitoring process is generated in the following manner.

The preparation of this calibration curve is illustrated for a detectable compound able to produce measurable luminescence before any chemical transformations in the CTFC. Known differing amounts of a particular detectable compound are (in the purposeful absence of any SC capable of interacting with the CTFC to cause a chemical transformation) prepared in a series of sample solutions. Each of these sample solutions is caused to electrochemiluminescence upon exposure to electrochemical energy in the form of a positive voltage bias imposed on an electrode of an electrochemiluminescent cell. The resulting experimentally measured luminescence is recorded. The predetermined luminescence standard for monitoring techniques comprises a calibration curve having experimentally measured luminescence on a first axis and known amounts of the particular detectable compound on the second axis. By comparing the experimentally measured luminescence of a solution containing a known quantity of the detectable compound and also containing a sample suspected of containing any second compounds with the corresponding luminescence value from the calibration curve, the CTFC is effectively monitored. Changes in the CTFC caused by interactions with any second compounds in the sample solution will result in measurable differences (deviations) from the calibration curve.

The monitoring processes can be used to screen suspected solutions for activity against the CTFC. Specifically, a series of sample solutions could be monitored with the detectable compounds. A positive electrochemiluminescence test result (i.e., a result that is either higher or lower than the predetermined standard) for any particular sample solution is indicative of at least one SC in that particular sample solution. Accordingly, that solution would then be an appropriate candidate for further detailed investigations.

The assaying processes are extensions of the monitoring processes in that the assaying processes are designed to specifically test for the presence and/or amount of a particular SC. As such, the assaying processes likewise are based on the chemical transformations in the CTFC which alter the effective intramolecular donating ability of the CT° FC to the EC.

By comparing (i) the measured luminescence of the detectable compound after the exposure of that detectable compound to a sample solution suspected of containing a particular SC that is capable of interacting with the CTFC and of effecting a chemical transformation in the CTFC with (ii) the measured luminescence of the predetermined standard, the particular SC is effectively assayed. More specifically, the presence and amount of the particular SC can be assayed. The predetermined luminescence standard of the assaying process is generated in the following manner.

Known amounts of a particular detectable compound are exposed to a series of sample solutions each containing known differing amounts of a particular SC that is capable of interacting with the CTFC of the detectable compound in accordance with the present invention. The exposure is effected under conditions favorable to and consistent with the desired interactions. Subsequent to such interactions, each of these sample solutions is caused to electrochemiluminescence and the experimentally measured luminescence is recorded. The predetermined luminescence standard for assaying processes comprises a calibration curve having experimentally measured luminescence on a first axis and known amounts of the particular SC on the second axis.

For both monitoring and assaying processes, the experimentally measured luminescence may be either greater than or less than the luminescence for the applicable predetermined luminescence calibration curve. In other words, the interaction between the CTFC and the at least one second compound may either increase or decrease the effective intramolecular electron donating ability of that CTFC (which would correspondingly increase or decrease the experimentally measured luminescence).

Preferred applications of the detectable compounds are monitoring and assaying processes when the CTFC first compound comprises a substrate and the SC comprises an enzyme that is specific to that substrate. Particularly preferred substrates are beta-lactams. Such beta-lactams are usefull in assaying processes that test for the corresponding beta-lactamase.

Another application of the detectable compounds of the present invention takes advantages of coupled, regenerative reaction mechanism that involve the conversion of a separate, nonconjugated substrate in solution into a separate, nonconjugated product in solution via exposure to an appropriate enzyme and co-mediators. The interactions between the CTFC and the enzyme-catalyzed, co-mediated conversion of a substrate species in solution to a product species in solution forms the theoretical underpinnings for an assay that can be specific to the substrate in solution, the enzyme in solution, and/or the CTFC.

Another use of the detectable compounds of the invention are in kits specifically designed to implement the processes of the present invention. Accordingly two types of kits are provided. The monitoring kits each comprise a plurality of sample standard solutions each containing known amounts of a particular detectable compound with the purposeful absence of any SC. These monitoring kits can be used to determine the predetermined luminescence standard calibration curve. The assaying kits each comprise a plurality of sample solutions each containing known amounts of a particular detectable compound in addition to a corresponding plurality of test solutions each containing known differing amounts of a particular SC that is capable of interacting with the detectable compound in the described manner.

(E) Examples.

Notwithstanding the previous detailed description of the present invention, applicants below provide specific examples solely for purposes of illustration and as an aid to understanding the invention. Particularly with respect to the protection to which the present invention is entitled to, these examples are both nonlimiting and nonexclusive.

Accordingly, the scope of applicants' invention as set forth in the appended claims is to be determined in light of the teachings of the entire specification without incorporating in such claims the specific limitations of any particular example.

Example 1

Figure 4:
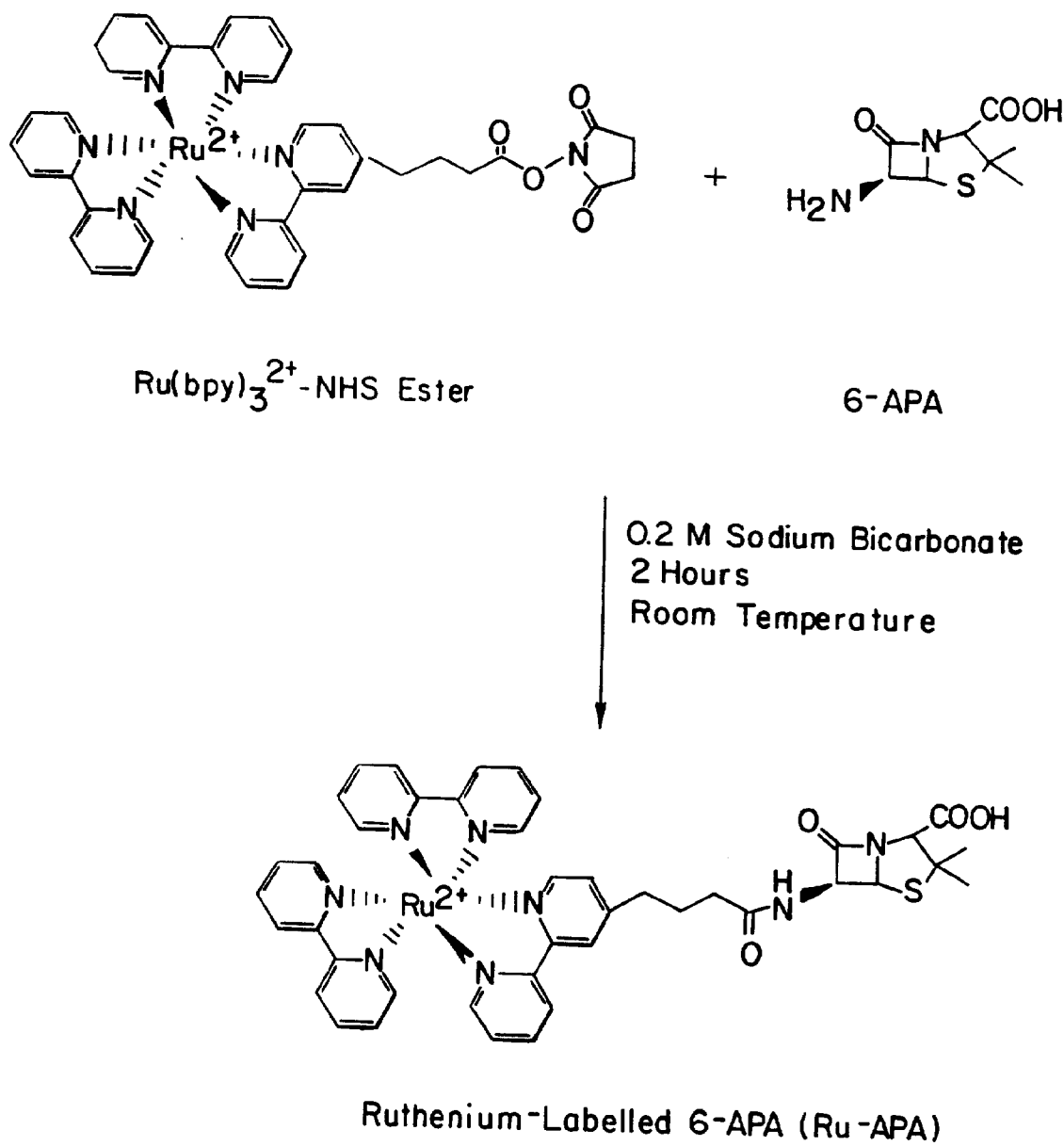
FIG. 4 shows the synthesis of Ru-AMP.
Figure 5:
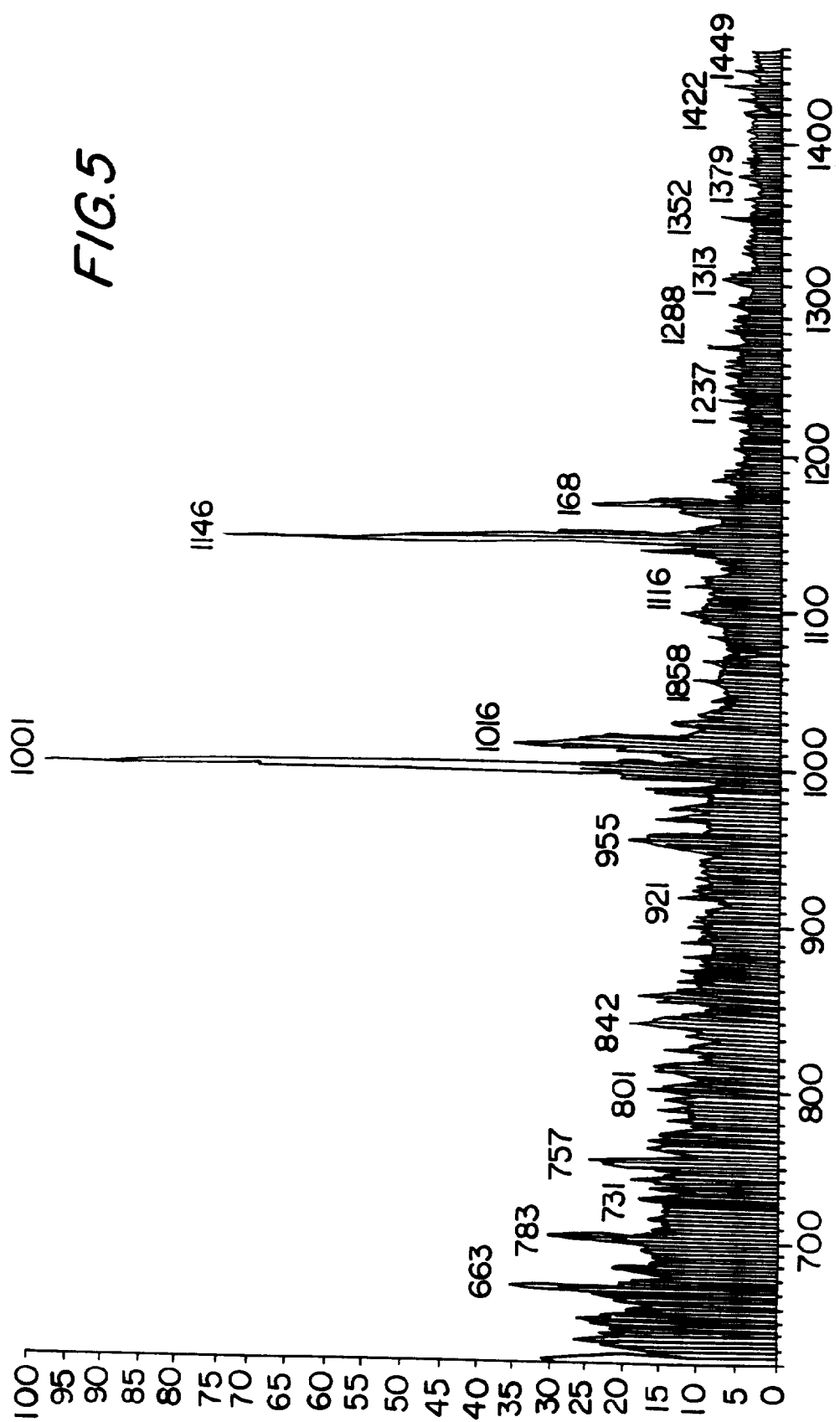
FIG. 5 shows the mass spectrum of the ammonium hexafluorophosphate salt of Ru AMP.
Figure 6:
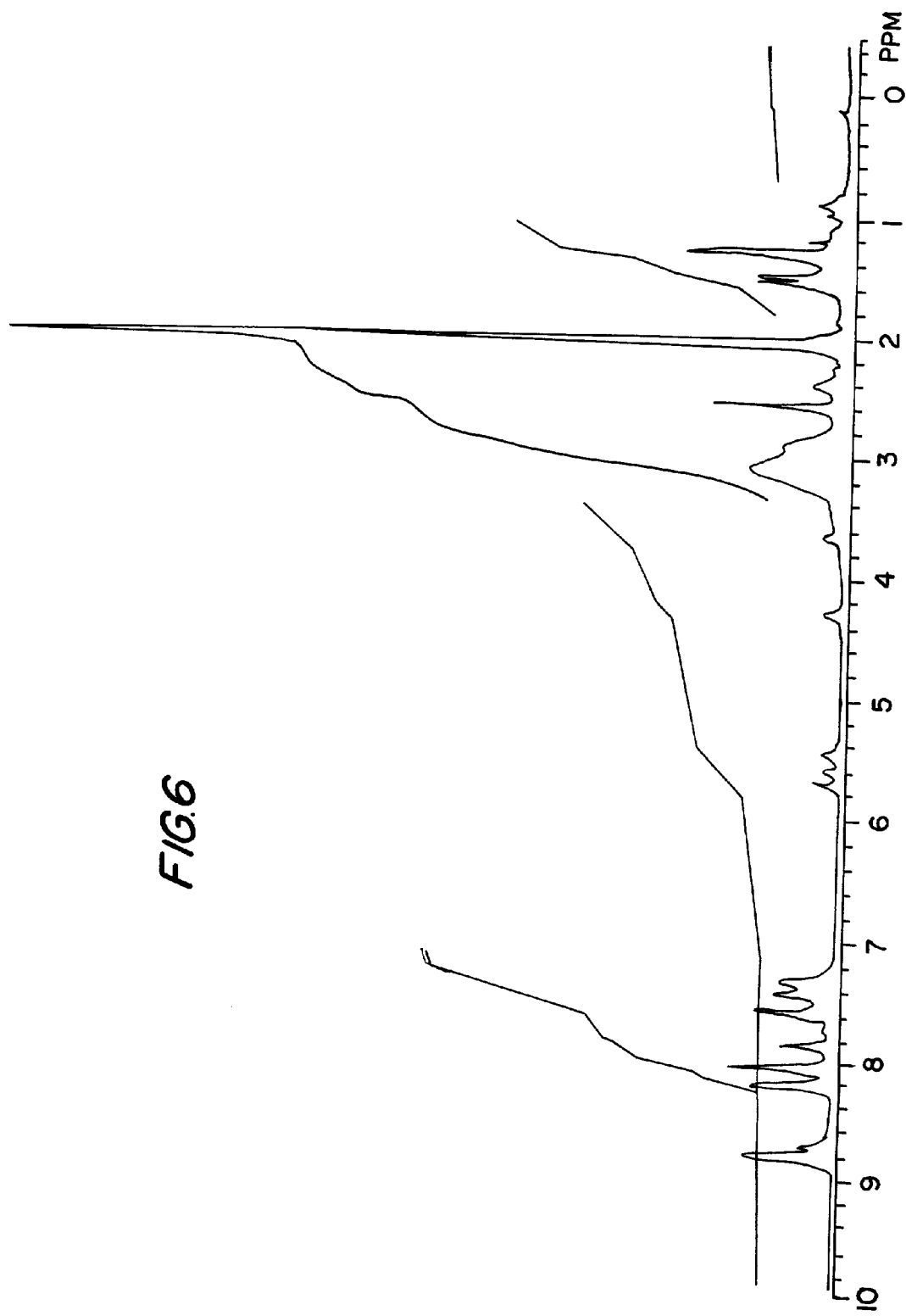
FIG. 6 shows the proton NMR spectrum of the ammonium hexafluorophosphate salt of Ru-AMP.
Figure 8B:
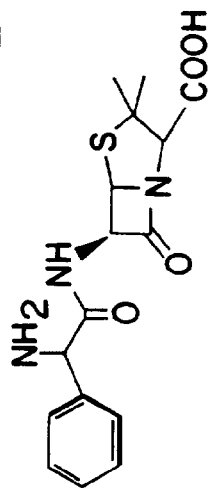
FIG. 8 shows the structures of 5 specific beta-lactams.
Figure 8D:
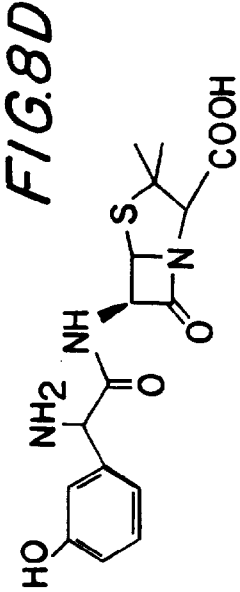
Figure 8A:
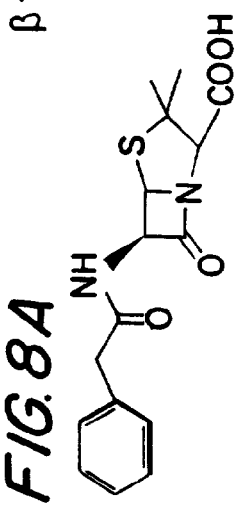
Figure 8C:
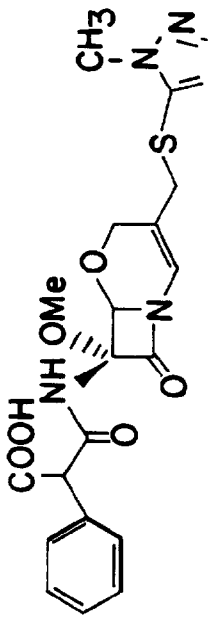
Figure 8E:
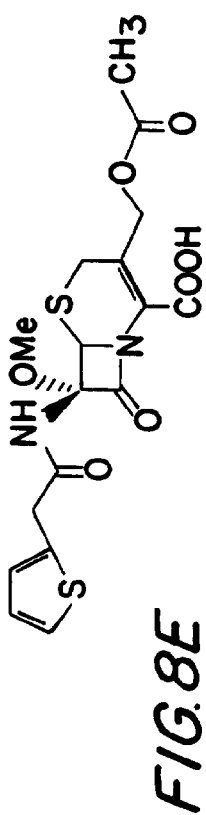

Preparation of Ru(bpy)$_3^{+2}$-labeled beta-lactum antibiotics (a) Preparation ofRu(bpy)$_3^{+1}$-labeled ampicillin (Ru AMP):

Ru(bpy)$_3^{+2}$-NHS ester (15.1) mg in acetonitrile (250 μL) was mixed with ampicillin (29.1 mg) in 0.2 M sodium bicarbonate, pH 8.0 (250 μL) and the reaction was allowed to proceed at room temperature for 2 hours (FIG. 4). Ru-AMP was purified using a Waters BPLC system (Milford, MA) equipped with a ProgelTm-TSJ CM-5PW column (7.5 cm×7.5 mm) (Supelco, Inc., Bellefonte, Pa.) using a 1.0 mL/minute, 15-minute linear gradient from 20–180 mM sodium phosphate, pH 7.0. Substrate was quantitated spectrophotometrically by measuring the absorbance of the ruthenium complex (the molar extinction coefficient at 453 nn is 13,700 $M^{-1}cm^{-1}$). Following formation of the ammonium hexafluorophosphate salt, the structure and purity of Ru-AMP was confirmed by mass spectroscopy and proton NMR (FIGS. 5–6).

(b) Preparation of Ru(bpy)$_3^{+2}$-labeled 6-aminopenicillanic acid (hereinafter "Ru-APA")

Ru(bpy)$_3^{+2}$-NHS ester (15 mg) (IGEN, Inc., Gaithersburg, Md.) in acetonitrile (250 μL) was mixed with 6-aminopenicillanic acid (12.4 mg) in 0.2 M sodium bicarbonate, pH 8.0 (350 μL) and the reaction was allowed to proceed at room temperature for 2 hours (FIG. 7). Ru APA was purified with a Waters HPLC system (Milford, MA) equipped with a Progel™-TSK CM-SPW column (7.5 cm×7.5 mm) (Supelco, Inc., Bellefonte, PA) using a 1.0 mL/minute, 20-minute linear gradient from 20–100 mM sodium phosphate, pH 7.0. Substrate was quantitated spectrophotometrically by measuring the absorbance of the ruthenium complex (the molar extinction coefficient at 453 nm is 13,700 $M^{-1}cm^{-1}$).

(c.) Preparation of otherRu(bpy)$_3^{+2}$-labeled beta-lactams

Other beta-lactams, such as 7-aminocephalosporanic acid, that have a primary amine in their structures can also react with Ru(bpy)$_3^{+2}$-NHS ester to form similar conjugates as described above. The reaction and purification conditions will be similar, potentially differing somewhat in ways solvable by one skilled in the art. FIG. 8 shows the structure of 5 specific beta-lactams.

Example 2

ECL assay of Ru-AMP hydrolysis

Experiments were performed to compare the ECL properties of Ru-AMP (conjugated) with Ru(bpy)$_3^{+2}$ and ampicillin mixtures (nonconjugated). ECL properties were compared both before and after NaOH and enzymatic hydrolysis (FIG. 9, left side).

Ru-AMP was found to be a very good substrate of beta-lactamase. Hydrolysis of Ru-AMP (33 μM) by beta-lactamase I from *Bacillus cereus* (0.3 nM) was monitored spectrophotometrically at 240 run using a Hitachi U3200 spectrophotometer (Danbury, Conn.) at 25.0° C. in 0.1 M sodium phosphate, pH 7.0. Half-time ($t_{1/2}$) analysis gave a $k_{cat}/K_m$ for 2 enzymatic hydrolysis of Ru-AMP of $3.9\times10^8$ $min^{-1}M^{-1}$.

Figure 10:
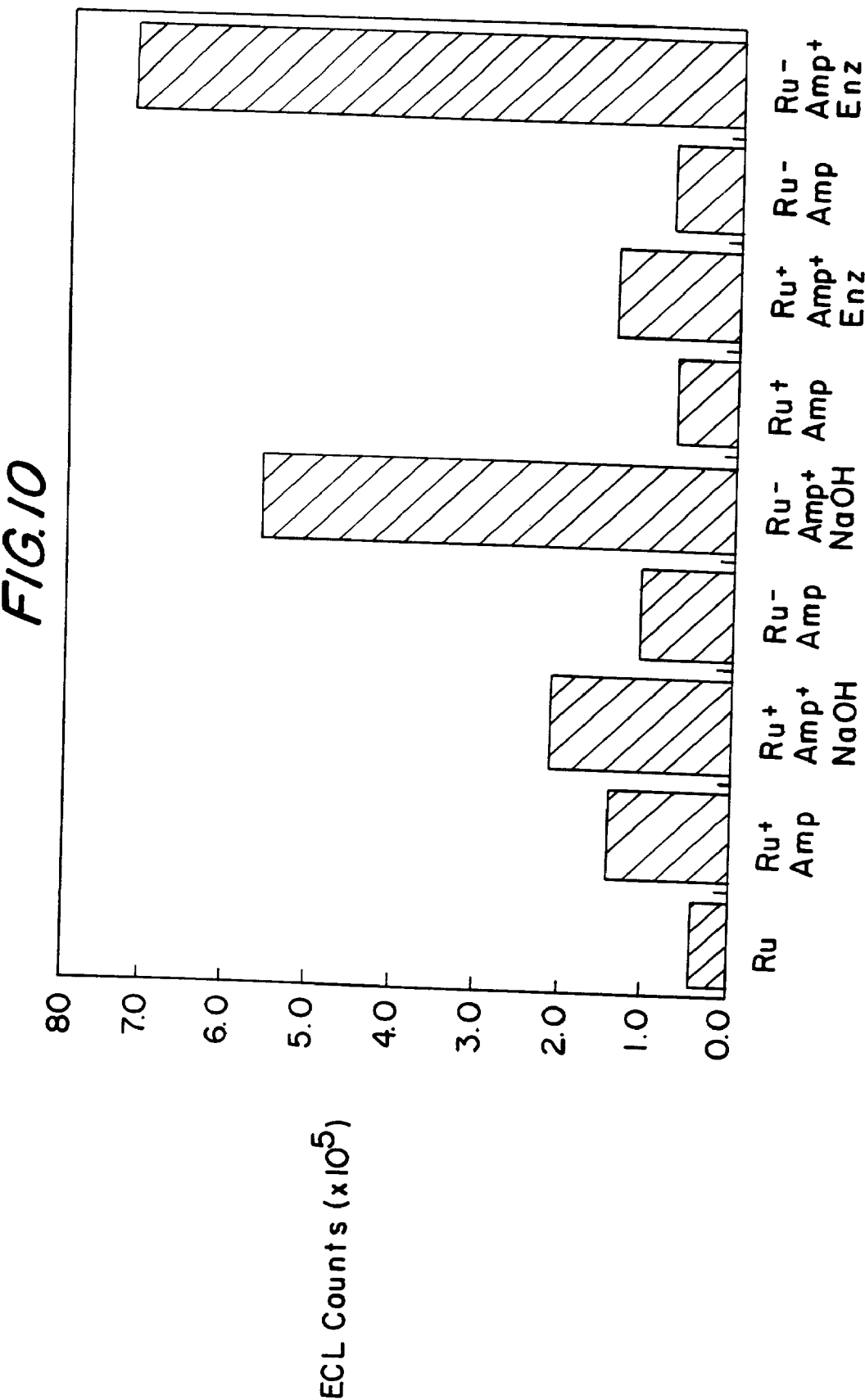
FIG. 10 shows the comparison of measured ECL for a series of different samples.

The ECL properties of equimolar mixtures of Ru(bpy)3$^{+2}$ and ampicillin (hydrolyzed or unhydrolyzed) were compared to the same concentration of the Ru-AMP conjugate (hydrolyzed or unhydrolyzed). In separate experiments, ampicillin and Ru-AMP were hydrolyzed by either 250 mM NaOH (base hydrolysis) or 441 nM beta-lactam I from *Bacillus cereus* (enzyme hydrolysis). For base hydrolysis, 50 μL of 5 M NaOH were added to 1.0 mL solutions of deionized water containing either 24.85 μM Ru-AMP or a mixture of 25 μM ampicillin and 25 μM Ru(bpy)$_3^{+2}$. Following 30 minute incubations, the solutions were neutralized with 50 μL of 5 M HCl. For the unhydrolyzed counterpart experiments, 50 μL of $H_2O$ were added to solutions of either 24.85 μM Ru-AMP or a mixture containing 25 μM ampicillin and 25 μM Ru(bpy)$_3^{+2}$. Following 30 minute incubations, 50 μL of 5 M NaCl was added to these solutions. The results shown in FIG. 10 demonstrate: (1) that ampicillin hydrolysis by either NaOH or beta-lactamase causes an increase in the ECL of the mixtures; and (2) that the increase in the ECL caused by the hydrolysis is dramatically greater when the light-emitting ruthenium complex is covalently linked to ampicillin. With base hydrolysis, ECL increased 1.5-fold when ampicillin was hydrolyzed in a mixture of ampicillin and Ru(bpy)$_3^{+2}$, while ECL increased 5.2-fold when Ru AMP was hydrolyzed. Similar results were obtained in enzyme hydrolysis: ECL increased 2.1 fold when ampicillin was hydrolyzed in a mixture of ampicillin and Ru(bpy)$_3^{+2}$, while ECL increased 9.8-fold upon hydrolysis of Ru-AMP. The data establishing these conclusions is found in FIG. 10 which shows the experimentally measured electrochemiluminescence of (from left to right):

Ru(bpy)$_3^{+2}$ alone;

Ru(bpy)$_3^{+2}$ plus unhydrolyzed ampicillin;

Ru(bpy)$_3^{+2}$ plus NaOH-hydrolyzed ampicillin;

unhydrolyzed Ru-AMP;

NaOH-hydrolyzed Ru-AMP;.

Ru(bpy)$_3^{+2}$ plus unhydrolyzed ampicillin;

Ru(bpy)$_3^{+2}$ plus beta-lactamase-hydrolyzed ampicillin;

unhydrolyzed Ru-AMP; and beta-lactamase-hydrolyzed Ru-AMP.

Figure 11:
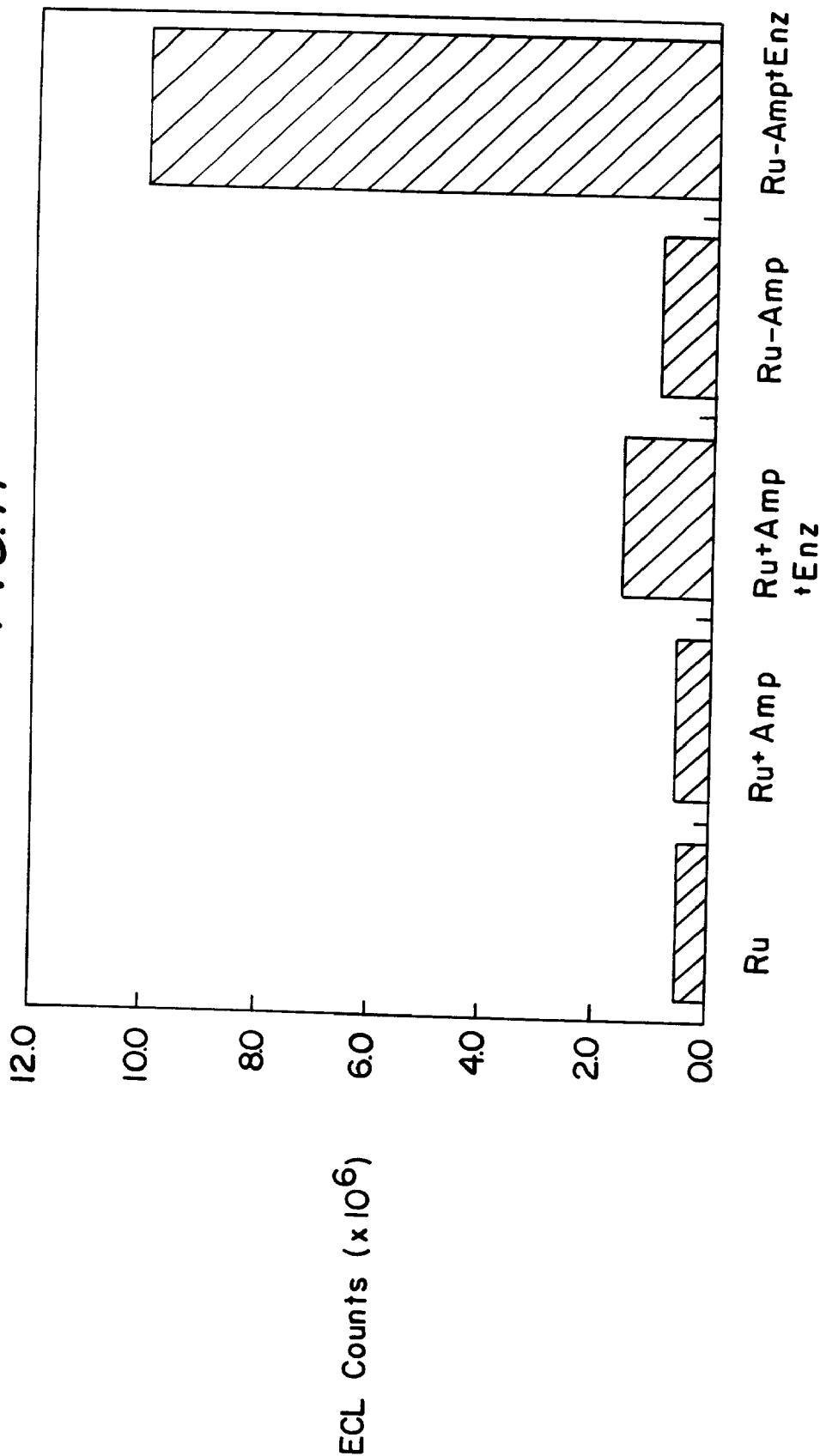
FIG. 11 shows the comparison of measured ECL for a series of different samples.

This work was confirmed in a second experiment using enzyme hydrolysis which differed in that the incubation time with enzyme was lengthened from 30 to 60 minutes (FIG. 11). Here, enzyme hydrolysis caused a 2.5-fold increase in ECL when ampicillin and Ru(bpy)$_3^{+2}$ were unconjugated and an 11.1-fold increase in ECL when the Ru-AMP conjugate was hydrolyzed. The data establishing these conclusions is found in FIG. 11 which shows the experimentally measured luminescence of(from left to right):

Ru(bpy)$_3^{+2}$ alone;

Ru(bpy)$_3^{+2}$ plus unhydrolyzed ampicillin;

Ru(bpy)$_3^{+2}$ plus beta-lactamase-hydrolyzed ampicillin;

unhydrolyzed Ru-AMP; and beta-lactamase-hydrolyzed Ru-AMP.

These results show that Ru(bpy)$_3^{+2}$-conjugation caused intramolecular effects that dramatically increase the experimentally measured luminescence when the beta-lactam ring is hydrolyzed.

Figure 12:
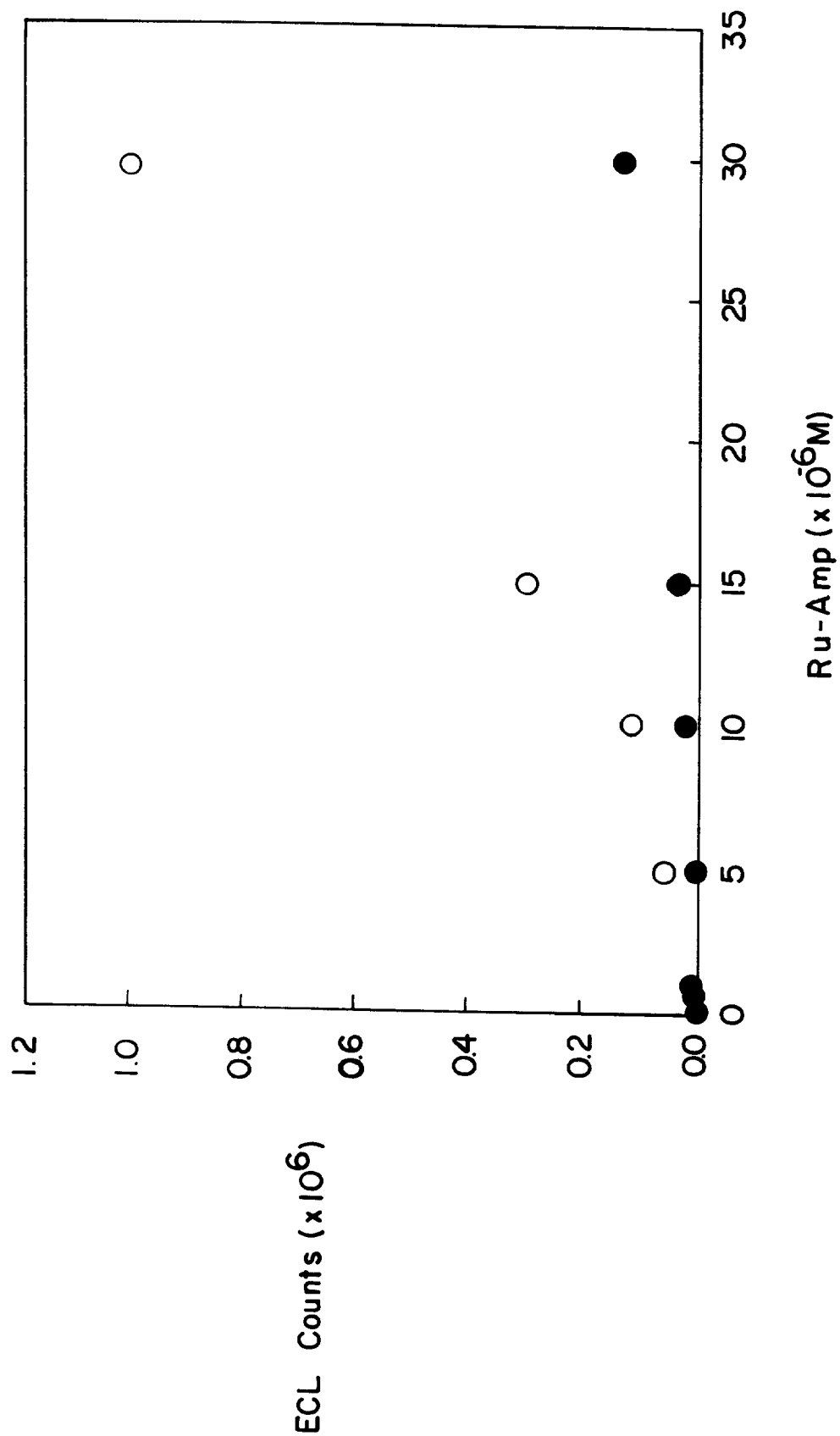
FIG. 12 shows the effect of unhydrolyzed (closed circles) and hydrolyzed (open circles) Ru-AMP concentration on the measured ECL.

FIG. 12 shows that low concentrations of Ru-AMP can be detected by hydrolysis. The lower limit of detection was found to be 50 nM (464 relative ECL counts for hydrolyzed Ru-AMP versus an average instrument reading of-1 52 relative counts for unhydrolyzed Ru-AMP). This compares favorable to the lower limit for detection of (unconjugated) ampicillin hydrolysis which was 5000 nM.

Example 3

ECL assay of Ru APA hydrolysis

It was thought that Ru-APA might have different ECL properties (before and after hydrolysis) from those of Ru-AMP. The differences would be a consequence of the structural differences between APA and AMP, especially the difference in distance between the beta-lactam ring and the primary amino group used to conjugate Ru(bpy)$3^{+2}$-NHS ester (FIG. 9, right side). In Ru-AMP, the beta-lactam ring is three bond lengths farther from the amino group than in Ru-APA. Specifically, hydrolysis of Ru-APA (or other beta lactam conjugates) may be more or less sensitively detected by ECL than Ru-AMP hydrolysis.

The ECL properties of the Ru-APA conjugate were compared with those of the mixtures is of unconjugated Ru(bpy)$_3^{+2}$ and 6-APA. ECL properties were compared before and after NaOH and enzymatic hydrolysis. The data was then compared to the results of similar experiments with Ru-AMP described in Example 2.

Ru-APA was found to be a very good substrate of beta-lactamase. Hydrolysis of Ru-APA (23 $\mu$M) by beta-lactamase I from *Bacillus cereus* (0.6 nM) was monitored spectrophotometrically at 240 nm using a Hitachi U3200 spectrophotometer (Danbury, CT) at 25.0° C. in 0.1 M sodium phosphate, pH 7.0. Half-time ($t_{1/2}$) analysis gave a $k_{cat}/K_m$ for enzymatic hydrolysis of Ru-APA of 9.8×10$^7$ min$^{-1}$M$^{-1}$. This rate indicates that the enzyme hydrolyzed Ru-APA with a 4-fold lower efficiency than Ru-AMP, but that Ru-APA hydrolysis by beta-lactamase is still exceptionally efficient.

The ECL properties of equimolar mixtures of Ru(bpy)$_3^{+2}$ and APA (hydrolyzed or unhydrolyzed) were compared with the same concentration of the Ru-APA conjugate (hydrolyzed or unhydrolyzed). In separate experiments, 6-APA and Ru-APA were hydrolyzed by either 250 mM NaOH (base hydrolysis) or 347nM beta-lactamase I from *Bacillus cereus* (enzyme hydrolysis).

Figure 13:
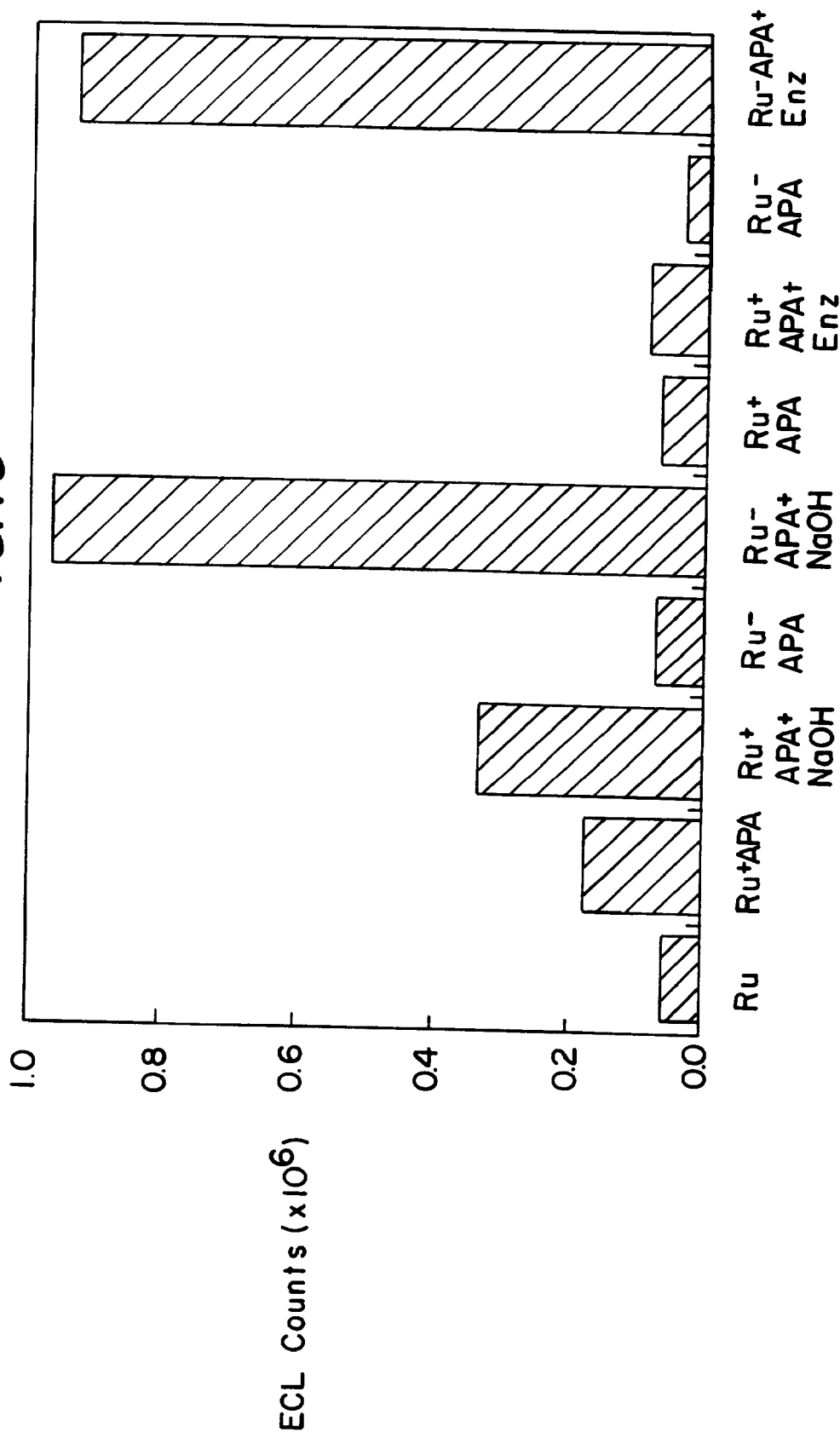
FIG. 13 shows the comparison of measured ECL for a series of different samples.

For base hydrolysis, 50 $\mu$L of 5 M NaOH were added to 1.0 mL solutions of deionized water containing either 23.0 $\mu$M Ru-APA or a mixture containing 23.0 $\mu$M APA and 23.0 $\mu$M Ru(bpy)$_3^{+2}$. Following 60 minute incubations, the solutions were neutralized with 50 $\mu$L of 5 M HCL. For unhydrolyzed counterpart experiments, 50 $\mu$L of H$_2$0 were added to solutions of either 23.0 $\mu$M Ru-APA or a mixture of 23.0 $\mu$M APA and 23.0 $\mu$M Ru(bpy)$_3^{+2}$. Following 60-minute incubations, 50 $\mu$l, of 5 M NaCI was added to these solutions. The results shown in FIG. 13 demonstrate: (1) that 6-APA (conjugated or nonconjugated) hydrolysis by either NaOH or beta-lactamase causes an increase in ECL; and (2) that the increase in ECL caused by hydrolysis is dramatically greater when the light-emitting ruthenium complex is covalently coupled to 6-APA. With base hydrolysis, ECL increased 1.9-fold when 6-APA (nonconjugated) in a mixture of 6-APA and Ru(bpy)$_3^{+2}$ was hydrolyzed, while ECL increased 13.2-fold when Ru-APA (conjugated) was hydrolyzed. Similarly with enzyme hydrolysis, ECL increased 1.4-fold when 6-APA (nonconjugated) in a mixture of 6-APA and Ru(bpy)$_3^{+2}$ was hydrolyzed, while ECL increased 31.8-fold when Ru-APA (conjugated) was hydrolyzed. The data establishing these conclusions is found in FIG. 13 which shows the experimentally measured luminescence of (from left to right):

Ru(bpy)$_3^{+2}$ alone;

Ru(bpy)$_3^{+2}$ plus unhydrolyzed 6-APA;

Ru(bpy)$_3^{+2}$ plus NaOH-hydrolyzed 6-APA;

unhydrolyzed Ru-APA;

NaOH-hydrolyzed Ru-APA;

Ru(bpy)$_3^{+2}$ plus unhydrolyzed 6-APA;

Ru(bpy)$_3^{+2}$ plus beta-lactamase-hydrolyzed 6-APA;

unhydrolyzed Ru-APA; and beta-lactamase-hydrolyzed APA.

This work clearly demonstrates that conjugation of the 6-APA and the electrochemiluminescent ruthenium complex result in intramolecular effects that increase the electrochemiluminescence when the beta-lactam ring is hydrolyzed. Moreover, comparison with the results described in Example 2 for the ampicillin conjugate show that hydrolysis of Ru-APA results in a much greater electrochemiluminescence signal than hydrolysis of Ru-AMP. Because the ruthenium atom is closer to the beta-lactam ring in Ru-APA than in Ru-AMP, these results indicate that there may be a critical effect of the distance between the ruthenium complex and the beta-lactam ring. Other, as-yet untested beta-lactam-Ru (bpy)$_3^{+2}$ conjugates may give an even more dramatic change in the electrochemiluminescence upon beta-lactam hydrolysis.

Figure 14:
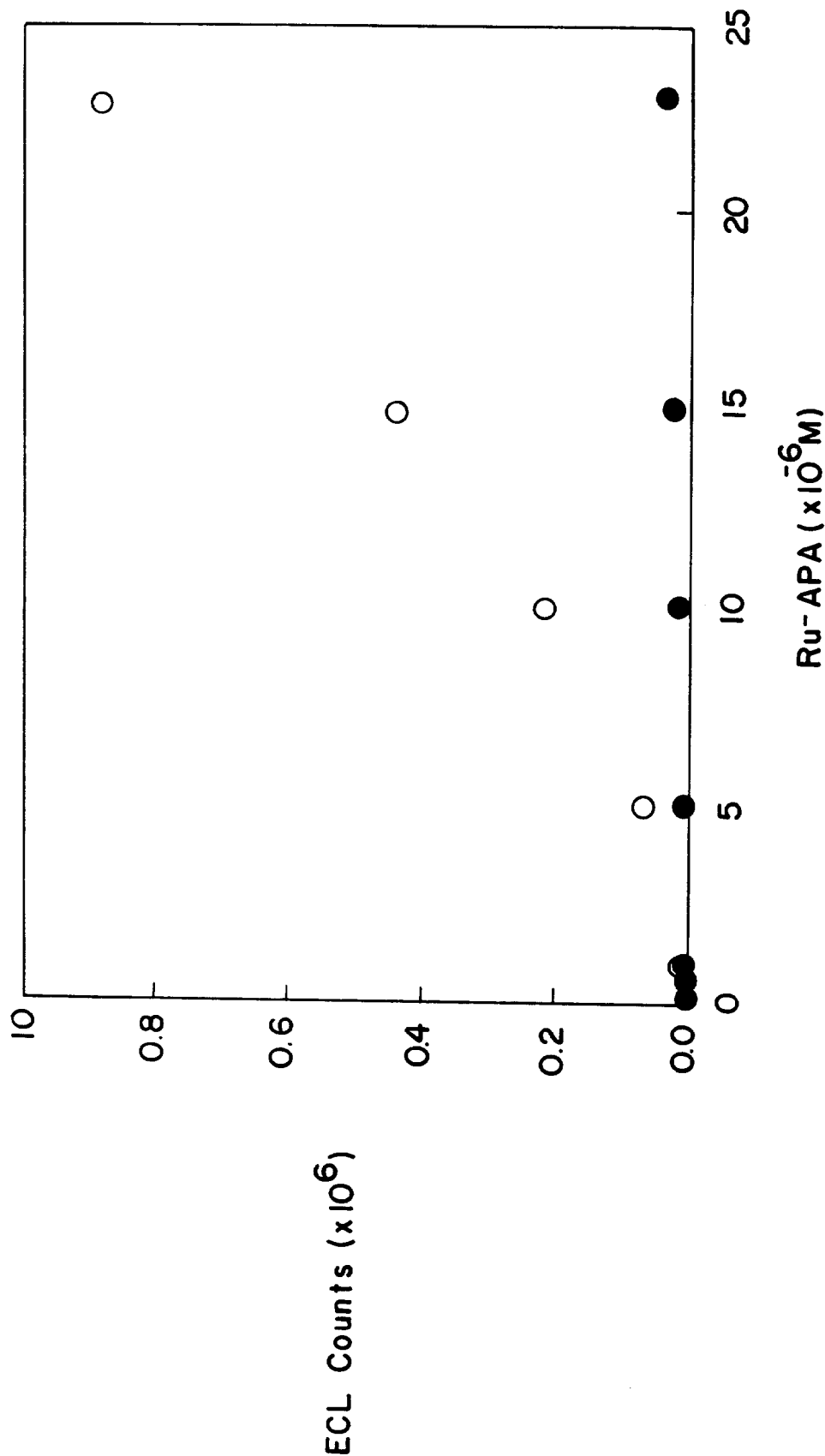
FIG. 14 shows the effect of unhydrolyzed (closed circles) and hydrolyzed (open circles) Ru-APA concentration on the measured ECL.

FIG. 14 shows that the hydrolysis of very low concentrations of Ru-APA can be detected by ECL. More specifically, FIG. 14 shows the effect of unhydrolyzed (closed circles) and hydrolyzed (open circles) Ru-APA concentration on the experimentally measured electrochemiluminescence. The lower limit of detection was found to be 50 nM (an instrument reading of −33 relative ECL counts for hydrolyzed Ru-APA versus an average of −b48 relative ECL counts for unhydrolyzed Ru-APA (conjugated)). This compares favorably to the lower limit for detection of (unconjugated) APA hydrolysis which was 50 $\mu$M (in the presence of 10 $\mu$M Ru(bpy)$_3^{+2}$).

Figure 15:
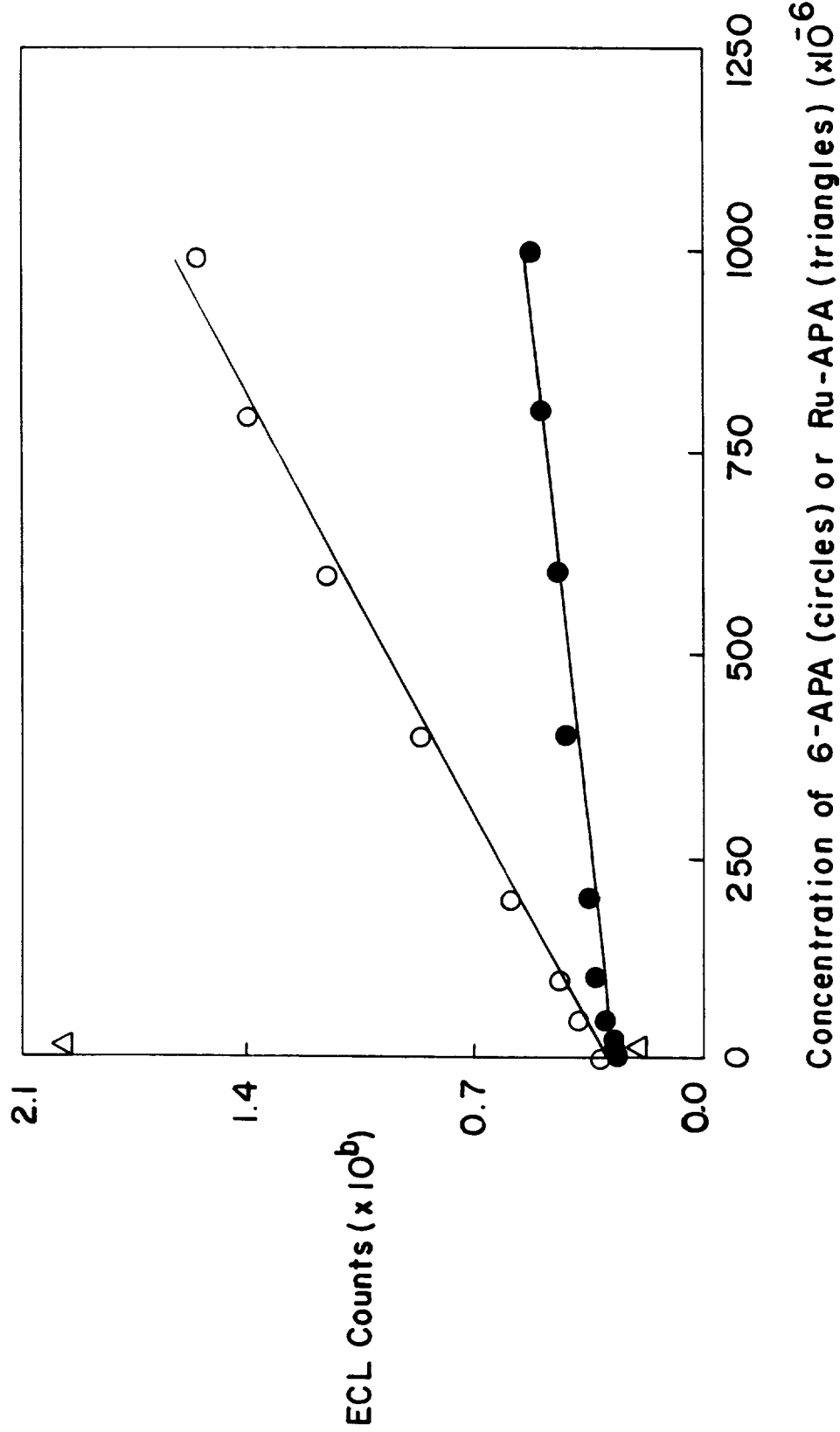
FIG. 15 shows the comparison of measured ECL for a series of different samples.

An experiment was performed to quantitate the advantage of conjugating a beta-lactam to the ECL label, Ru(bpy)$_3^{+2}$. The increase in ECL upon hydrolysis of 10 $\mu$M Ru-APA was compared to an ECL standard curve in which various concentrations of 6-APA (nonconjugated) were hydrolyzed in the presence of 10 $\mu$M Ru(bpy)$_3^{+2}$. By extrapolation of the 6-APA standard to curve, the results (FIG. 15) demonstrates that the ECL change upon hydrolysis of 10 $\mu$M Ru-APA (conjugated) is equivalent to the ECL change in the hydrolysis of 1250 $\mu$M 6-APA (nonconjugated) in the presence of 10 $\mu$M Ru(bpy)$_3^{+2}$. This demonstrates that conjugation of Ru(bpy)$_3^{+2}$ and 6-APA results in a 125-fold increase in the ECL change seen during 6-APA hydrolysis. The data establishing these conclusions is found at FIG. 15 which shows a comparison of electrochemiluminescence effects of Ru-APA (conjugated) to Ru(bpy)$_3^{+2}$ plus 6-APA (unconjugated). Triangles represent the electrochemiluminescence of 10 $\mu$M unhydrolyzed (open triangles) and hydrolyzed (closed triangles) Ru-APA. Circles represent the electrochemiluminescence effects of unhydrolyzed (closed circles) and hydrolyzed (open circles) 6-APA (0–1000 $\mu$M) in the presence of 10 $\mu$M Ru(bpy)$_3^{+2}$. Extrapolation in FIG. 15 indicates the electrochemiluminescence change upon hydrolysis of 10 $\mu$M Ru-APA is equivalent to the electrochemiluminescence change upon hydrolysis of 1250 $\mu$M free 6-APA in the presence of 10 $\mu$M Ru(bpy)$_3^{+2}$.

Example 4

Preparation of Ru(bpy)$_3^{+2}$-labeled β-nicotinamide adenine cofactors (a) Theory of Oxidoreductase Enzymes and Their Use in Assays β-Nicotinamide adenine cofactors (such as NAD$^+$, NADH, NADP$^+$, NADPH) are widely used in nature by oxidoreductase enzymes as oxidants or reductants during reduction or oxidation of metabolites. Such enzymes include many dehydrogenases (lactate dehydrogenase, alcohol dehydrogenase, glucose dehydrogenase, etc.). The oxidized forms of these cofactors (NAD$^+$ or NADP$^+$) have little or no TPA-like effects in ECL. However, the reduced forms (NADH or NADPH) behave like TPA in promoting Ru(bpy)$_3^{+2}$ electrochemiluminescence (1, 2). Consequently, ECL can be used to measure the enzyme-catalyzed formation or disappearance of the reduced forms of these cofactors. Hence, substrates (glucose, ethanol, etc.) of dehydrogenases can be detected by ECL since their chemical transformations by the appropriate enzyme stoichiometrically results in oxidation or reduction of nicotinamide adenine cofactors.

Figure 16:
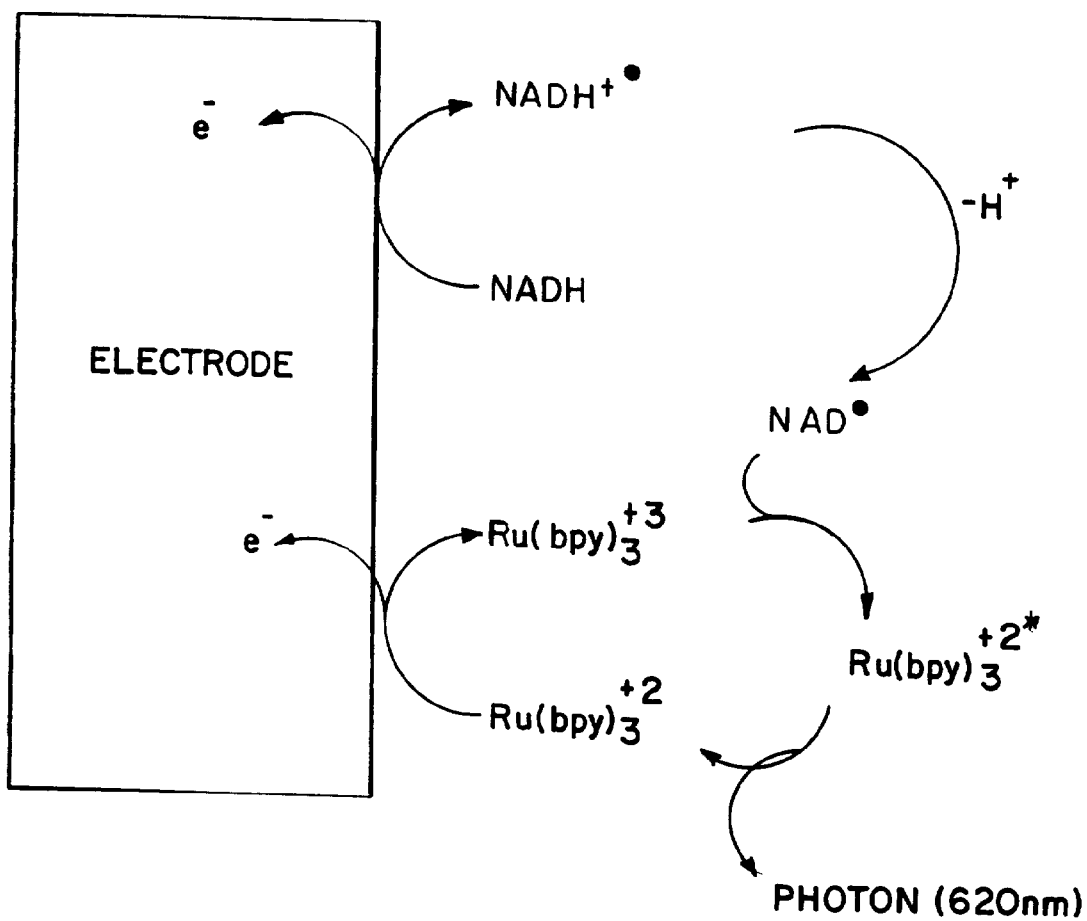
FIG. 16 shows a proposed ECL mechanism depicting reaction steps associated with the NADH-promoted ECL of Ru(bpy)3$^{+2}$.

Reduced nicotinamide cofactors (NADH or NADPH) are not believed to be destroyed during the ECL reactions as are TPA and beta-lactams, but are instead converted to their oxidized forms (NAD$^+$ or NADP$^+$). This means that, in the presence of an appropriate dehydrogenase enzyme, nicotinamide adenine cofactors can be reused such that a single cofactor molecule that is covalently linked to an electrochemiluminescent compound can participate in multiple ECL reactions (FIG. 16). Note also in FIG. 16 that the Ru(bpy)$_3^{+2}$ is also regenerated so that it is possible for a single detectable compound comprising such a cofactor covalently linked to an electrochemiluminescent compound can possibly emit multiple photons one after another.

Nicotinamide adenine cofactors have advantages over present electrochemiluminescent techniques that use TPA. Specifically, these cofactors (i) can participate in regenerative ECL reaction mechanisms; (ii) can be used to detect and quantitate dehydrogenases and their corresponding substrates. One disadvantage is that the ECL signal (i.e., the experimentally measured luminescence) is less in an ECL reaction with NADH or NADPH than in an ECL reaction with TPA. This disadvantage could be reduced or obviated by using a conjugate of derivatives of Ru(bpy)$_3^{+2}$ and the nicotinamide adenine cofactor. As shown in the Examples above, when Ru(bpy)$_3^{+2}$ is conjugated to a chemically-transformable first compound which can act as a high energy reductant and intramolecularly donate an electron to the covalently linked—electrochemiluminescent compound (such as a beta-lactam), the ECL signal generated is much greater than when the CTFC is not conjugated with the EC. Similarly, a Ru(bpy)$_3^{+2}$-nicotinamide adenine cofactor (reduced form) conjugate will also have more ECL than a nonconjugated mixture of Ru(bpy)$_3^{+2}$ and the reduced cofactor. Similarly, the difference in ECL signal between the reduced (NADH or NADPH) and oxidized forms (NAD$^+$ NADP$^+$) the cofactors will be greater when the cofactors are covalently linked to the Ru(bpy)$_3^{+2}$ than when they are not conjugated.

Figure 17:
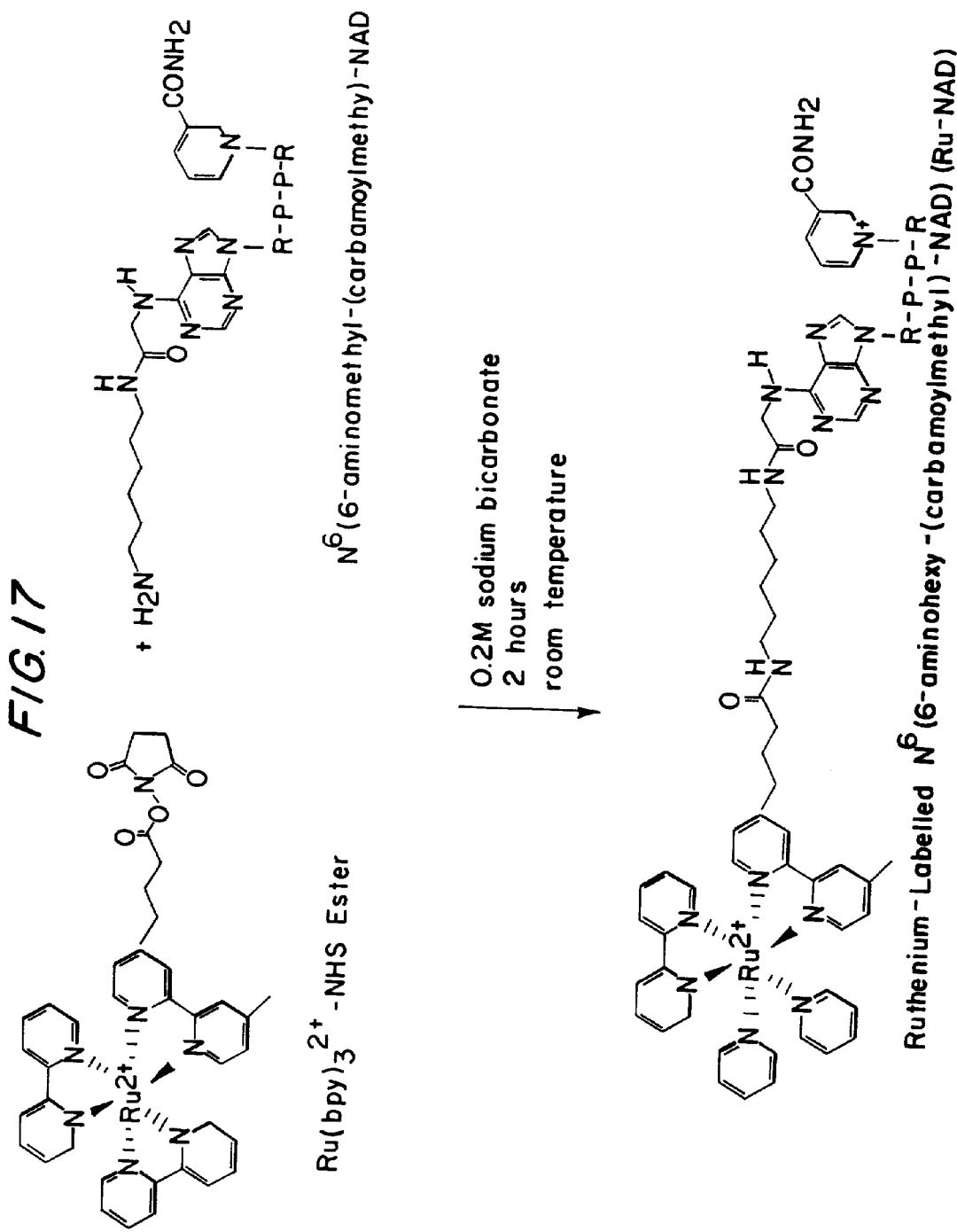
FIG. 17 shows the synthesis of Ru-NAD.
Figure 19C:
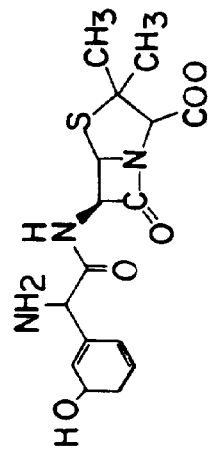
FIG. 19 shows chemical structures of some common B-lactams.
Figure 19B:
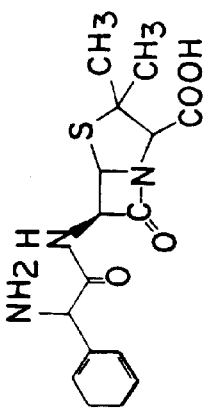
Figure 19A:
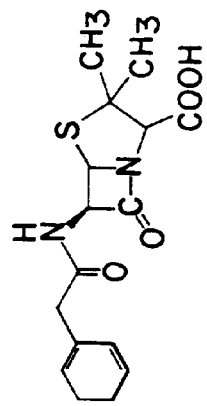
Figure 19E:
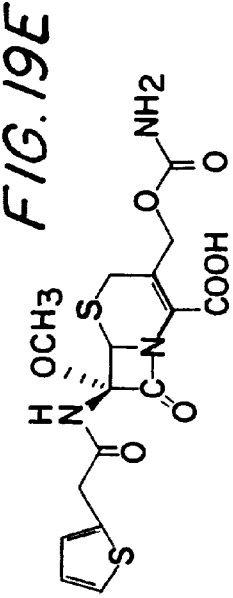
Figure 19D:
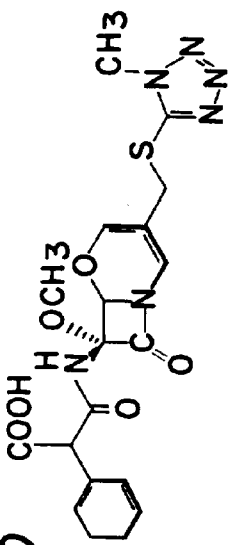
Figure 19H:
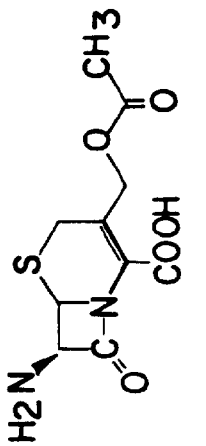
Figure 19G:
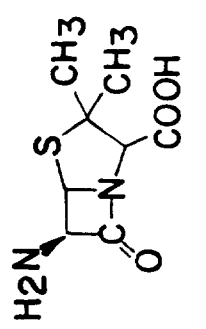
Figure 19J:
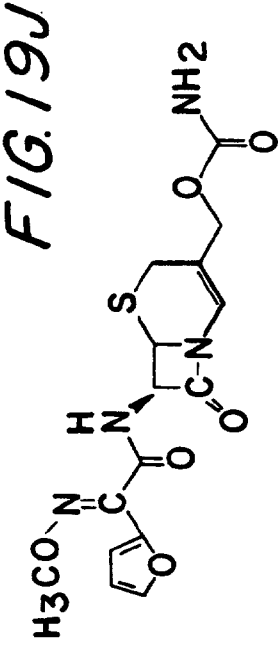
Figure 19F:
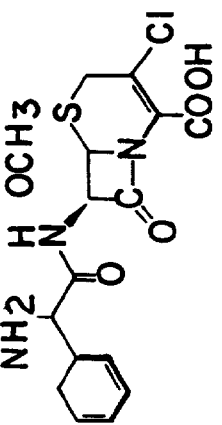
Figure 19I:
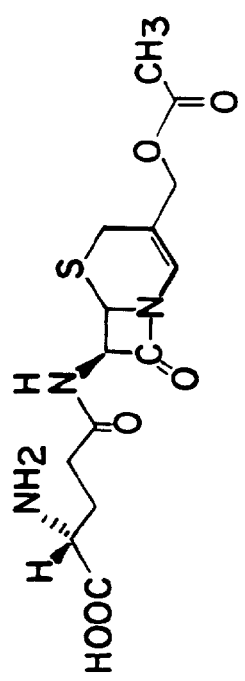
Figure 20A:
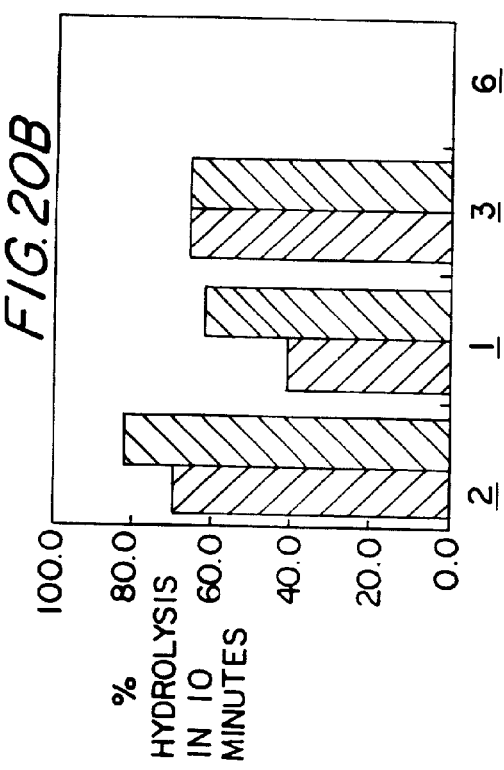
FIG. 20A shows *B. cereus* β-lactamase I (1.3 nM).
Figure 20B:
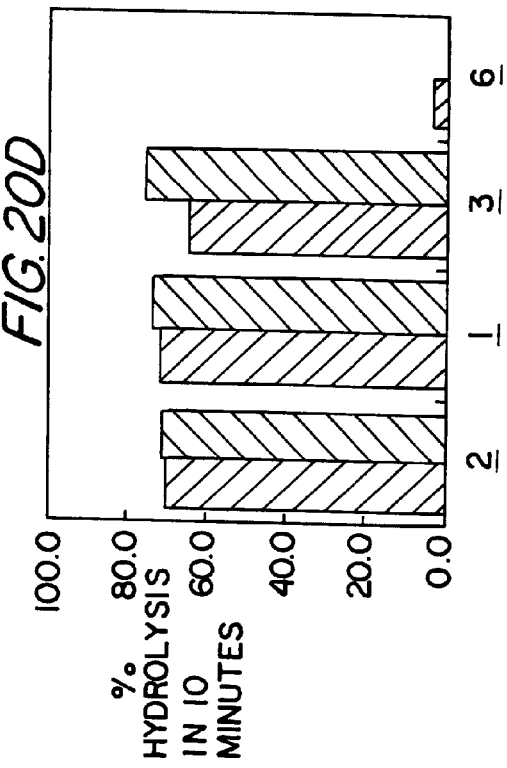
FIG. 20B shows *B. cereus* β-lactamase II (42.6 nM).
Figure 20C:
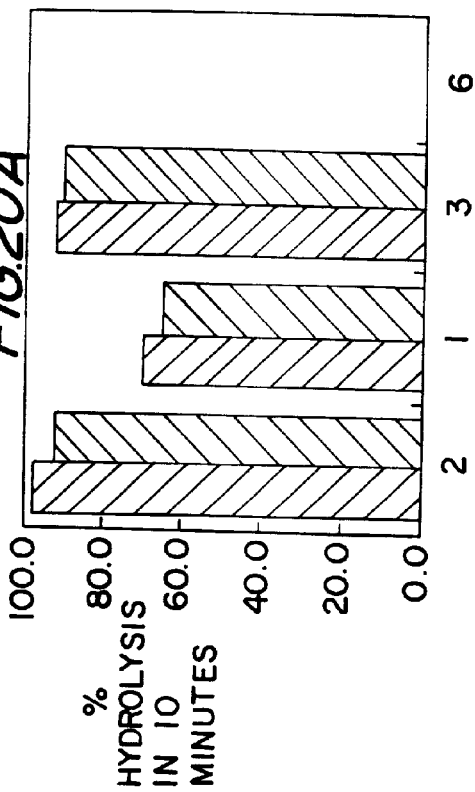
FIG. 20C shows Enterobacter cloacae P99 (1.9 nM).
Figure 20D:
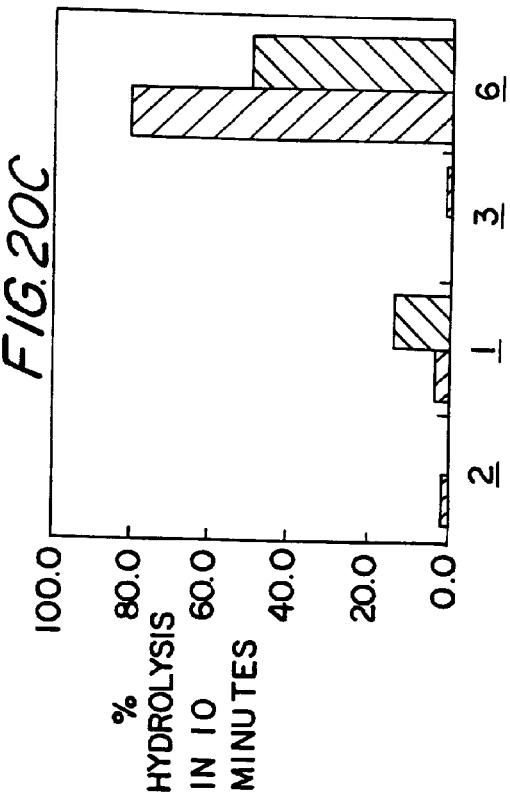
FIG. 20D shows *E. coli* RTEM (0.73 nM). For ECL experiments, 275 μL of each sample was mixed with 25 μL of 120 μM Ru(bpy)$_3^{2+}$ and 0.6% Triton X-100. The mixtures were analyzed using an ECL instrument (Origen™ Analyzer, IGEN, Inc., Rockville, Md.).

Conjugates of nicotinamide adenine cofactor derivatives are known and are enzymatically functional (3,4). One such cofactor derivative, N$^6$-([6-aminohexyl] carbamoylmethyl) nicotinamide adenine dinucleotide, is commercially available (Sigma Chem. Co., St. Louis, Mo.). The primary amino group of this compound can be used to couple this compound to the same Ru(bpy)$_3^{+2}$-NHS ester described above (obtainable from IGEN, Inc., Gaithersburg, Md.) by the same or similar method (FIG. 17) (3,4). Other similar coupling methods will also work. The conjugate (Ru-NAD) can be purified by HPLC in a similar manner as described for purification of Ru-AMP and Ru-APA. The four references noted above are (1) Downey, T. M. & Nieman, T. A. (1992) Anal. Chem. 64, 261–268; (2) Martin, A. F. & Nieman, T. A. (1993) Anal. Chem. Acta. 281, 475–481; (3) Mansson, M.-O., Larsson, P.-O., & Mosbach, K. (1982) Methods Enzym 89, 457–468; and (4) Persson, M., Mansson, M. O., Bulow, L., Mosbach, K. (1991) Bio/Technology 9, 280–284. Each of these four references is incorporated by reference. FIG. 17 shows the preparation of Ru-NAD.

The oxidized form of Ru-NAD (Ru-NAD$^+$) can be used in enzyme assays in an ECL instrument to detect and quantitate a dehydrogenase enzyme or a substrate of a dehydrogenase (or some compound that gives rise to either). The assays will be performed according to to conventional protocols (duration, temperature, pH, buffer, salt, substrate and enzyme concentrations, etc.) except that NAD$^+$ normally included will be excluded and Ru-NAD$^+$ will be used in place. The concentration of Ru-NAD$^+$ may be lower or higher than the conventional assays owing to differences in substrate specificity, solubility, cost, or other factors. Following the incubation, the mixture will be analyzed in an ECL instrument (IGEN, Inc., Gaithersburg, Md.). No additional Ru(bpy)$_3^{+2}$ will be added. Reduction of Ru-NAD$^+$ will be recognized by an increase in ECL signal over background and will indicate the presence of the relevant dehydrogenase and substrate.

Similarly, oxidation of the reduced form of Ru-NAD (Ru-NADH) can be detected by ECL. Again, conditions, and the presence of relevant enzyme and enzyme substrate will be considered and will be derived from known conditions for assays involving nonconjugated NADH. NADH will be omitted from the assay and Ru-NADH (at an appropriate concentration that may not be the conventional concentration) will be included. Following incubation, the mixture will be analyzed with an ECL instrument. Any decrease in ECL from the initial Ru-NADH signal will indicate that some Ru-NADH has been oxidized and will be evidence of the presence of the relevant enzyme or substrate.

(b) Preparation of Ruthenium-Labelled N$^b$[6-aminohexyl-(carbamoylmethyl)-NAD$^+$ To a solution containing 6.6 mg N$^6$[6-aminohexyl-(carbamoyhnethyl)-NAD$^+$ (Li$^+$ salt, Sigma Chem. Co., St. Louis, Mo.) in 0.4 niL of a 1:1 mixture of acetonitrile and NaHCO$_3$ (0.2 M, pH 8.6) was added an NHS ester of Ru(bpy)$_3^{+2}$ (IGEN, Inc., Gaithersburg, MD) in 0.2 mL of a 1:1 mixture of acetonitrile and NaHCO$_3$ (0.2 M, pH 8.6). The reaction mixture was run overnight at room temperature. The following morning, the reaction was stopped, the solvent removed, and the compound was purified by size exclusion chromatography (BioRad Bio-Gel P-2, BioRad Laboratories, Richmond, Calif.). Proton NMR showed the compound to be correct, but not completely pure. The compound (Ru-NAD) was repurified on a column of Sp-Sephadex (Pharmacia, Uppsala, Sweden), eluting with changes of increasing concentrations of trifluoroacetic acid (0, 0.05, 0.2, 0.3 M). NMR showed to compound to be pure Ru-NAD.

(c) Ru-NAD as an Enzyme Cofactor

To determine whether Ru-NAD was functional as an enzyme cofactor, a reaction involving oxidation of D-glucose-6-phosphate by glucose-6-phosphate dehydrogenase was tested. The reaction was monitored spectrophotometrically at 340 nm. This wavelength is commonly used to observe the interconversion of NAD$^+$ and NADH. A mixture of 63 µM Ru-NAD, 400 µM glucose-6-phosphate, and 22 µM enzyme in 55 mM Tris buffer, pH 7.8 containing 33 MM MgCl$_2$ was incubated at 30° C. in a cuvette. Continuous absorbance readings showed that absorbance increased over approximately 40 minutes in a fashion characteristic of enzymatic reduction of NAD$^+$. This indicated that Ru-NAD was indeed accepted as a functional cofactor by glucose-6-phosphate dehydrogenase.

(d) Effect of Enzymatic Reduction on the ECL of Ru-NAD

Ru-NAD was found to be accepted as a cofactor by the dehydrogenase, glucose-6-phosphate dehydrogenase. An experiment was performed involving oxidation of glucose-6-phosphate by this enzyme with concurrent reduction of Ru-NAD. Here, ECL measurements were made to determine if; (1) the ECL-inducing effects of NADH (but not NAD) are also present in Ru-NADH (but not Ru-NAD) and (2) if conjugation of Ru(bpy)$_3^{+2}$ with NADH causes an increase in ECL measurement sensitivity as compared to the ECL of a mixture of unconjugated Ru(bpy)$_3^{+2}$ and NADH. The results are shown below (all solutions contain the substrate, glucose-6-phosphate, solutions not containing Ru-NAD contained 1.0M Ru(bpy)$_3^{+2}$)

| Sample | ECL counts |
| --- | --- |
| 21 µM NAD$^+$ | 45,500 |
| 21 µM NAD$^+$ + enzyme | 45,200 |
| 21 µM NADH | 47,900 |
| 21 µM NADH + enzyme | 40,800 |
| 21 µM Ru-NAD | 71,700 |
| 21 µM Ru-NAD + enzyme | 132,000 |

These results show that addition of enzyme to Ru-NAD increases the ECL signal. Also the results show that, at unconjugated NAD concentrations too low for ECL effects to be seen, Ru-NAD clearly gives a large amount of ECL when enzyme is added. In conclusion, Ru-NAD behaves in the same way as free Ru(bpy)$_3^{+2}$ plus free NAD$^+$ in an ECL instrument (enzyme addition causes an increase in ECL), but Ru-NAD is much more sensitively detected. This indicated that low concentrations of dehydrogenases or their substrates can be sensitively detected by ECL of Ru-NAD$^+$ reduction or Ru-NADH oxidation.

II. ELECTROCHEMILUMINESCENCE ASSAY

Mechanism of ECL excitation is as follows. Ru(bpy)$_3^{2+}$ and antibiotic (hydrolyzed and/or unhydrolyzed) are oxidized at the surface of a gold electrode, forming Ru(bpy)$_3^{3+}$ and antibiotic$^{+\bullet}$, respectively. In this description, antibiotic is either intact or hydrolyzed. The antibiotic$^{+\bullet}$ spontaneously loses a proton, forming antibiotics. The antibiotic$^{\bullet}$, a strong reductant, reacts with Ru(bpy)$_3^3+$, a strong oxidant, forming the excited state of the detectant, Ru(bpy)$_3^{2+*}$. The excited state decays to the ground state through a normal fluorescence mechanism, emitting a photon having a wavelength of 620 nm.

Organic compounds which are suitable electrochemical detectants include, for example, rubrene and 9,10-diphenyl anthracene. Many organometallic compounds are suitable electrochemical detectants, but of preferable use are Ru-containing compounds, such as ruthenium II tris-bipyridine chelate, and Os-containing compounds. Detectants useful in the presently disclosed invention can be found in U.S. Pat. No. 5,310,687, the contents of which are incorporated herein by reference.

These detectants are stable for long periods. In addition, the detectants are safe and relatively inexpensive. They give a highly characteristic signal and do not occur in nature. Measurements based on luminescence of such detectants are sensitive, fast, reproducible and utilize simple instrumentation. The signal is generated repeatedly by each molecule of the detectant, thereby enhancing the sensitivity with which these detectants may be detected. The preferred electrochemiluminescent detectants of the present invention are conveniently referred to herein as Ru(bpy)$_3^{2+}$. Various amounts of this detectant, or its equivalent, may be employed. It is also to be noted that these detectants can be used directly in the biological or food samples without pretreatment of sample.

The energy necessary for formation of the excited state arises from the large difference in electrochemical potentials of the Ru(bpy)$_3^{3+}$ and the antibiotic$^{\bullet}$. The excited-state Ru(bpy)$_3^{2+*}$ decays through a normal fluorescence mechanism, emitting a photon at 620 nm. This process regenerates the original form of the Ru(bpy)$_3^{2+}$, which is free to cycle multiple times through the reaction sequence. Each ECL-active detectant, therefore, can emit many photons during each measurement cycle, thereby enhancing detection.

Quantification of the Ru(bpy)$_3^{2+}$ detectant can be readily automated with relatively uncomplicated instrumentation. The heart of an instrument is the electrochemical flow-cell, containing the working electrodes and counter electrodes for initiation of the ECL reaction. Both of the electrodes are fabricated from gold, but other materials have been used with various degrees of success. A potentiostat applies various voltage waveforms to the electrodes, and a single photomultiplier tube (PMT) detects the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the detectant is quantified by applying a ramp voltage to the electrodes and measuring the emitted light. After the measurement, a high-pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. Measurements of the working electrode current and the ECL intensity are induced by the application of a triangle wave to the electrodes. The applied voltage as shown is actually the voltage measured at the Ag/AgCl reference electrode and includes the effects of a significant uncompensated resistance; consequently, the actual voltage applied at the working electrode is substantially less than that depicted. The triangle waveform rises from 565 to 2800 mV at a rate of 750 mV/s and then decreases at the same rate to 1000 mV. The current that flows in the cell is primarily the result of the oxidation of the β-lactam antibiotic and the hydrolysis of water. Oxidation of both the β-lactam antibiotic and Ru(bpy)$_3^{2+}$ becomes evident when the applied voltage reaches ~1100 mV and produces a luminescence. The intensity of the luminescence increases with the applied voltage until the antibiotic at the surface of the electrode is depleted, resulting in decreased intensity. The intensity of the observed luminescence is great enough that it can easily be measured with conventional PMTs operating either in photon-counting or current modes.

The sample to which the β-lactam of interest has been added is then placed in a measuring cell to obtain an initial reading. Typically the β-lactam of interest is added in concentrations between 10 micromolar and 1.0 millimolar. The electrochemiluminescent detectant is typically present at $10^6$M concentrations (range 1–15 $\mu$M). The sample containing cell is then incubated for a sufficient period of time to insure that β-lactamase catalyzed hydrolysis can occur if the enzyme is present. This period of time typically varies between 5 minutes and 2 hours. Longer and shorter periods of time are possible depending on sample and reagent concentrations. Since all that is involved is empirical parameters, their values can be determined using conventional techniques.

Figure 21A:
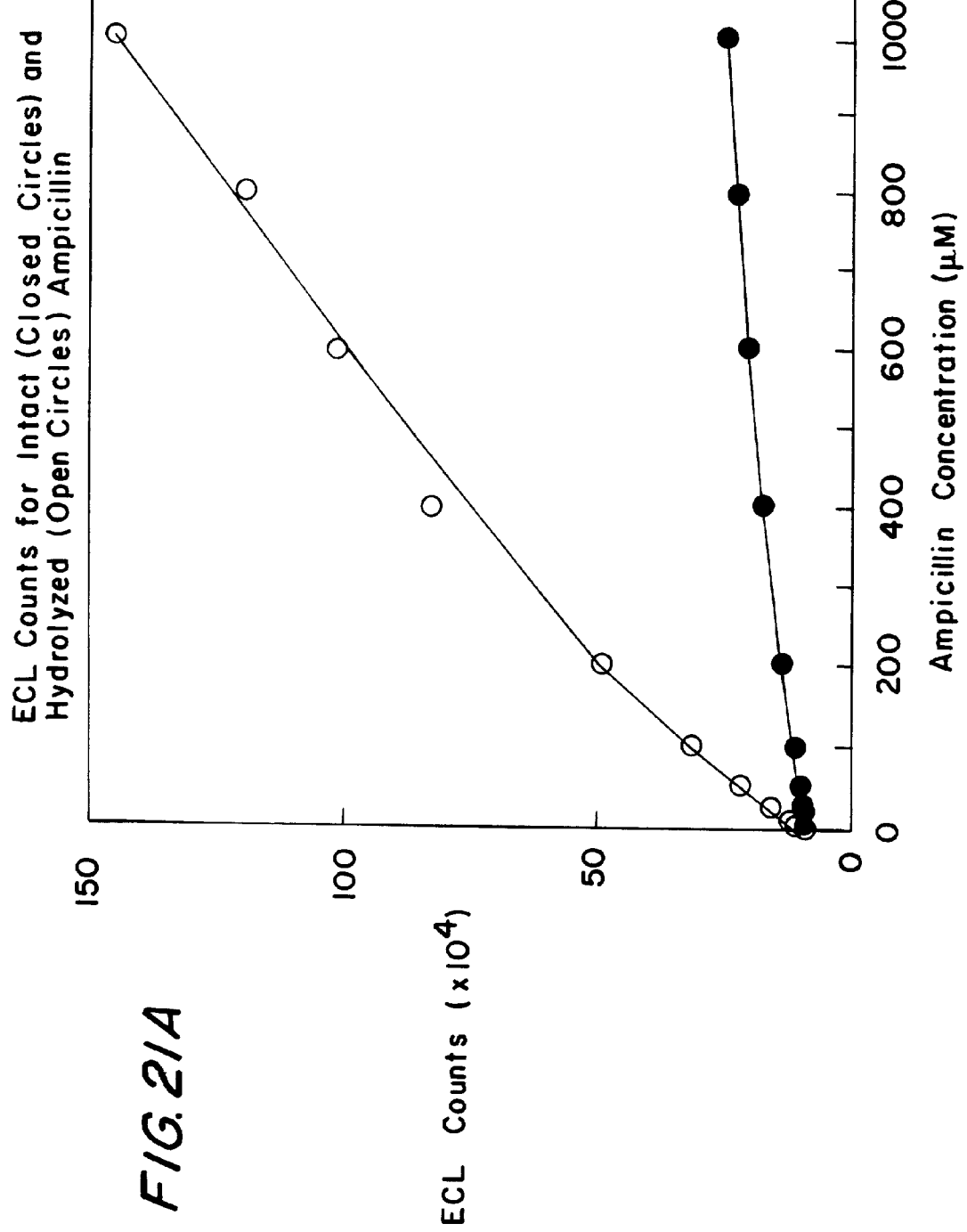
FIG. 21: Standard curves of hydrolyzed and unhydrolyzed β-lactam concentration versus ECL. Figure A shows enzyme-catalyzed (*B. cereus*) p-lactamase hydrolysis of ampicillin. Figure B shows NaOH hydrolysis of cefoxitin. In both A) and B) the closed circles represent the intact antibiotic and the open circles represent the products of antibiotic hydrolysis. Samples were treated and analyzed as described in the legend for FIG. 3.

After incubation occurs, a second reading is taken. The difference in readings, if any, correlates with β-lactamase activity present in the sample. See FIG. 21 in this regard. In a similar fashion, a particular sample can be subdivided or a series of samples can be taken from a particular patient and sequentially treated with a series of β-lactam antibiotics to generate a profile for the sample or patient. This profile can be used by a physician to select a preferred antibiotic for treatment or be used to identify the microorganism involved based on an existing library of information. The preferred antibiotic for use in treating an infection is the one least hydrolyzed.

Also possible is the creation of a set of standards obtained by repeating the method above with a series of antibiotics using a β-lactamase from a series of representative β-lactamases. Such a representation is shown in FIGS. 20 *a–d*. Values determined for an unknown can be compared against such a set for identification purposes. This information can be in electronic form to facilitate handling and comparison.

After the sample is treated with β-lactam antibiotic and/or incubated, the ECL measurement is performed by application of electrical potential to the working electrode. This gives a characteristic signal from the emitted light. Relatively little interference results from background presented by the other materials present in the sample or added buffer.

Accordingly, the apparatus and methodology suitable for the performance of the process of this invention include, as noted earlier, those shown in US. Pat. Nos. 5,068,088, 5,061,455, 5,093,268, and 5,147,806 and 5,221,605, which patents are expressly incorporated herein by reference. In addition, electrochemiluminesence molecules for use in the measuring system as detectants include those bidentate aromatic heterocyclic nitrogen-containing ligands of ruthenium and osmium described in U.S. Pat. Nos. 5,310,687 and 5,310,687, which patents are expressly incorporated herein by reference.

Reagent kits containing the materials necessary for the performance of the assays can be assembled to facilitate handling, and foster standardization. Materials to be included in the kit may vary depending on the ultimate purpose. Typically the kit would include the electrochemiluminescent detectant, necessary buffers, and standards. The standards can be chemical reagents or data (empirical) in printed or electronic form necessary for the calibration necessary for performance of the assay.

Example 1

ECL Assay of β-Lactam Hydrolysis by β-Lactamases

Bacterial β-lactamase enzymes hydrolyze and inactivate β-lactam antibiotic substrates FIG. 1). There are over 100 β-lactamases produced by many different species of gram negative and gram positive bacteria (1). Each β-lactamase will hydrolyze a limited and unique "spectrum" of β-lactam antibiotics (for structures of some β-lactam antibiotics, see FIG. 2). Thus, if a β-lactamase-producing bacterial strain is challenged with an antibiotic that is not a substrate of its β-lactamase(s), the antibiotic may be lethal. Conversely, if a bacterial strain is challenged with a β-lactam antibiotic that is a substrate of its β-lactamase(s), that strain will destroy the antibiotic, resist the challenge, and survive. It is difficult to predict in advance whether a pathogenic microbe produces a β-lactamase and, if so, which antibiotics that particular enzyme recognizes and hydrolyzes. It would greatly benefit medical treatment of such microbial infections if, as part of the physician's decision-making process, a sample of a patient's infected tissue or biological fluid could be mixed with candidate antibiotics prior to antibiotic administration to determine whether a β-lactamase is present capable of hydrolyzing the antibiotic and rendering it ineffective.

In one experiment, hydrolysis (or lack thereof) of six different commercially-obtained β-lactam antibiotics (benzylpenicillin, 1; ampicillin, 2; amoxycillin, 3; moxalactam, 4; cefoxitin, 5; and cephalosporin C, 6) by one or more of four different β-lactamases was detected and quantitated using an electrochemiluminescence (ECL)-based method. The antibiotics differ significantly in chemical structure, although each has in common the four-membered β-lactam ring (FIG. 2). Each antibiotic was dissolved to a concentration of 1.0 mM in a pH 7.5 solution of 0.1 M phosphate (sodium salt) containing of 10 $\mu$M ruthenium (II) tris(bipyridyl) (abbreviated as Ru(bpy)$_3^{2+}$), and 0.05% Triton X-100. Other solutions of the antibiotics were made that were identical except that they also contained one of four commercially-obtained β-lactamase enzymes (either 1.3 nM Type I from *Bacillus cereus*, 42.6 nM Type II from *Bacillus cereus*, 0.73 nM RTEM from *E. coli*, or 1.9 nM Enterobacter cloacae P99). Following 10-minute incubations at room temperature (approximately 22° C), ECL analyses of the antibiotic solutions (with and without each enzyme) were performed using an ECL-analyzing instrument (Origen$^R$ Analyzer, IGEN, Inc., Rockville, Md.). The effects of enzyme incubation on the ECL intensity were observed.

For verification of the source of generated ECL, hydrolysis of the same six antibiotics was also monitored spectrophotometrically (spectral changes are-known to occur in the ultraviolet region upon hydrolysis of β-lactam antibiotics). Spectrophotometric analysis of antibiotic hydrolysis actually consisted of multiple methods because the UV spectral properties of the six antibiotics differ substantially. The wavelength monitored in each assay as well as the cuvette path length required individual optimization for each antibiotic; benzylpenicillin and ampicillin required a 10 mm cuvette and a wavelength of 240 nm, cephalosporin C required measurement a 2 mm cuvette and a wavelength of 260 nm, cefoxitin required a 2 mm cuvette and a wavelength of 265 nm, moxalactam required a 2 mm cuvette and a wavelength of 270 nm, and amoxicillin required a 2 mm cuvette and a wavelength of 240 nm. In contradistinction, ECL measurements were all made using identical ECL instrument settings.

The results, shown on FIGS. 20 *a–d*, demonstrated that β-lactam hydrolysis by low (nanomolar or less) concentrations of β-lactamases can be detected by ECL in 10 minutes. Hydrolysis of the antibiotics moxalactam and cefoxitin are not shown in FIG. 20 because both ECL and spectrophotometric methods demonstrated that they were not catalyzed by any of the enzymes used in the experiment (although treatment with base showed that substantial ECL changes accompany hydrolysis of these compounds, see Example 2).

FIG. 20 shows that quantitation of hydrolysis by spectrophotometric (black bars) and ECL (gray bars) assay methods give similar results. The results also demonstrate that each of the four enzymes tested has a unique "spectrum" of substrate specificity. Choice of a therapeutically-effective antibiotic in a clinical setting would favor one that is not significantly hydrolyzed by the microorganism's β-lactamase. Thus, this experiment can be thought of as a study of four "mock" infections. Each mock infection (enzyme) has been challenged with six candidate β-lactam antibiotics to determine β-lactamase substrate specificity, information that would assist in predicting each antibiotic's in vivo effectiveness.

Example 2

ECL Assay of Beta-Lactam Hydrolysis by Base

Beta-Lactam antibiotics can be hydrolyzed by acids or bases. Hydrolysis of β-lactam antibiotics with dilute sodium hydroxide generally yields experimentally identical ECL assay results as when they are hydrolyzed by β-lactamases (Table 1). In some cases where a particular β-lactam may not be recognized or hydrolyzed by any known β-lactamases, ECL quantitation of antibiotic can be made by comparison with the ECL characteristics of base-hydrolyzed samples of the antibiotic.

| Antibiotic (1.0 mM) | Hydrolyzing Agent | Hydrol./Unhydrol. ECL (Ratio of ECL Counts) |
| --- | --- | --- |
| Benzylpenicillin | Base | 18.0 |
|  | Enzyme | 15.5 |
| Ampicillin | Base | 5.8 |
|  | Enzyme | 5.3 |
| Amoxicillin | Base | 7.0 |
|  | Enzyme | 5.5 |

Table 2 shows the effect of NaOH on the ECL generated by the 10 β-lactams whose structures are shown in FIG. 19.

| Beta-Lactam | Hydrol./Unhydrol. ECL Ratio |
| --- | --- |
| Moxalactam | 25.7 |
| Benzylpenicillin | 18.0 |
| Amoxicillin | 7.0 |
| Ampicillin | 5.8 |
| 6-Aminopenicillanic acid | 5.4 |
| Cefaclor | 2.2 |
| Cefuroxime | 0.82 |
| Cephalosporin C | 0.40 |
| Cefoxitin | 0.38 |
| 7-Aminocephalosporanic acid | 0.33 |

Overnight treatment with 0.2 M NaOH resulted in complete hydrolysis of the β-lactam ring in every case. It can be seen that in all instances base hydrolysis changes the ECL properties, although to varying extents. Some of the antibiotics tested (such as penicillin G, ampicillin, and amoxicillin) gave increased ECL after hydrolysis while others (such as cefoxitin and cephalosporin C,) gave substantially less ECL after hydrolysis. There is a general trend that penicillins give more ECL after hydrolysis and cephalosporins give less ECL after hydrolysis, although there are no obvious chemical structural reasons for this observation or for the fact that each compound behaves uniquely. The underlying mechanistic reasons for the differences in ECL behavior are probably a result of variations in the susceptibilities of the substrates and products of the reactions to form stable radical cations that can efficiently transfer an electron to $Ru(bpy)_3^{3+}$ (see FIG. 6 which shows a scheme of proposed ECL mechanism).

It should be noted that in some cases (with cephalosporin C and cefaclor), results varied depending on the concentration of NaOH used to hydrolyze the antibiotic and the length of hydrolysis time. This is believed to be due to other reactions, in addition to β-lactam hydrolysis, that occur between NaOH and these specific compounds. Enzymatic hydrolysis is a chemically milder way of hydrolyzing β-lactams and in some cases may be preferred to the use of NaOH.

Example 3

Quantitation of β-Lactams by ECL

Figure 21B:
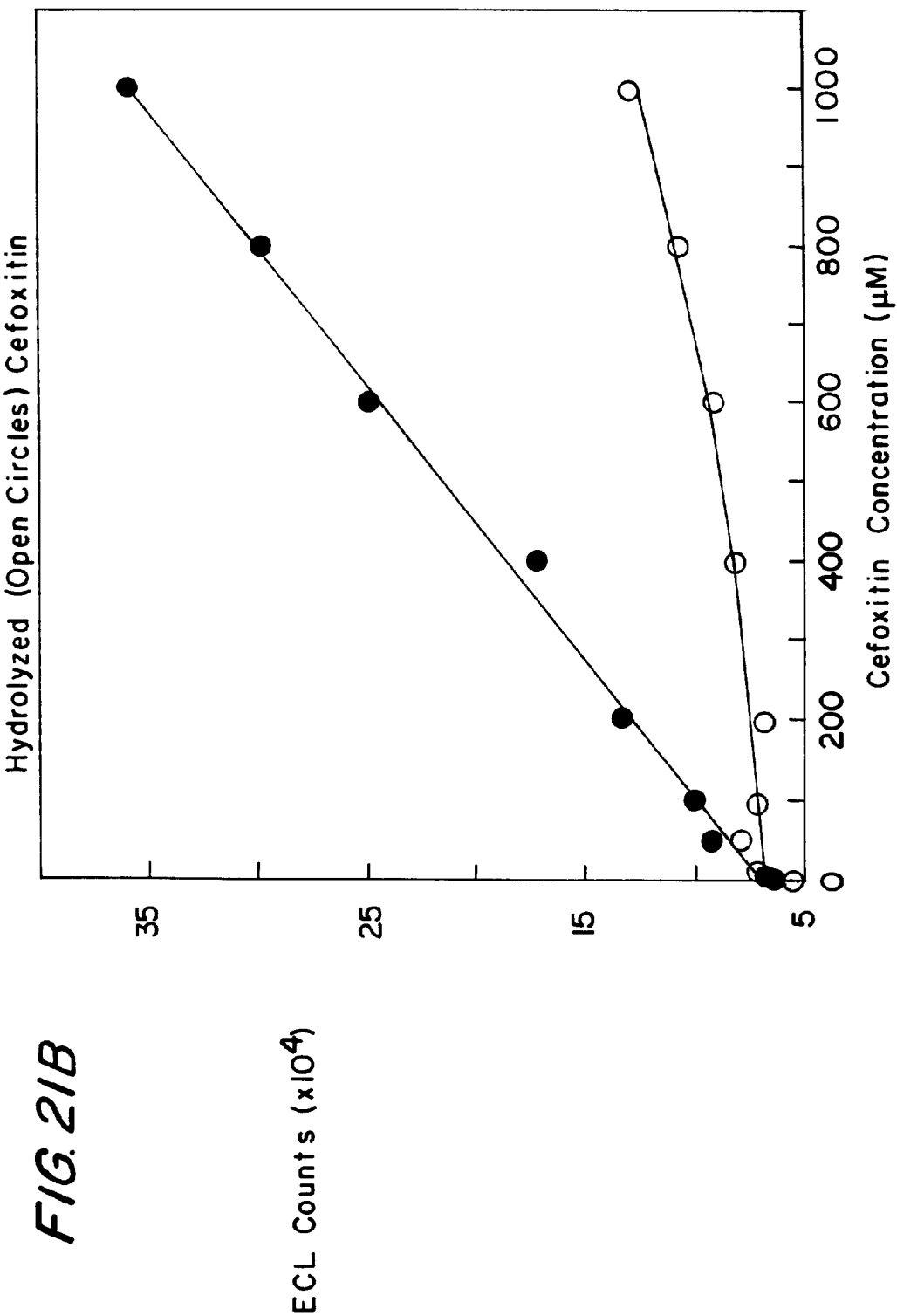

Determining the concentrations of β-lactam antibiotics is important in therapeutic drug monitoring and also in monitoring the quality of food such as meat and milk from cattle that have been administered antibiotics. For any analytical method, it is critical to show that the signal varies as a function of the analyte concentration. Detection and quantitation of lactams analyzed using ECL were found to be dependent on their concentrations such that the concentration of an unknown sample could be determined by comparison with an appropriate standard curve. Standard curves (antibiotic concentration vs. ECL) have been generated for penicillin G, ampicillin, amoxyciliin, cefoxitin, cephalosporin C, and moxalactam. Shown in FIG. 4 are standard curves for the commonly-used penicillin, ampicillin, (FIG. 21a) and for the widely-used cephalosporin, cefoxitin (FIG. 21b). In the case of ampicillin, 275 μL of various concentrations of the antibiotic (0–1.0 mM) were incubated in 0.1 M sodium phosphate, pH 7.5 for 10 minutes at room temperature in the absence or presence of 7 nM β-lactamase I from B. cereus (ampicillin). For cefoxitin, a 1.5 mM solution of the antibiotic was incubated in 0.2 M NaOH overnight at room temperature. Appropriate dilutions (275 μL of 0–1.0 mM) of the solution of hydrolyzed cefoxitin and of a comparable unhydrolyzed solution of cefoxitin were made. To 275 μL of the ampicillin and cefoxitin solutions (hydrolyzed and unhydrolyzed) was added 25 μL of a solution of 120 μM $Ru(bpy)_3^{2+}$ and 0.6% Triton X-100 and the samples were analyzed in an IGEN Origen™ ECL Analyzer. In general agreement with the data presented in Table 2 ampicillin hydrolysis resulted in an increase in ECL while cefoxitin hydrolysis caused a decrease in ECL. In both cases, a general trend was found that makes it possible to predict how much antibiotic would be present in a sample if the ECL was measured before and after appropriate hydrolysis.

Example 4

Quantitation of β-Lactamases by ECL

There are over 100 types of β-lactamase enzymes. Each has, under defined conditions of pH, temperature, and other factors, kinetic constants of substrate catalysis that are reproducibly characteristic of that particular enzyme. One kinetic constant that is especially important is the $k_{cat}$, defined as the maximum velocity ($V_{max}$) for catalysis of a given substrate per molecule of enzyme (for example, a $k_{cat}$ of $10s^{-1}$ means that one enzyme molecule will catalyze 10 substrate molecules per second at $V_{max}$). Thus, when an enzyme is operating at $V_{max}$ (which occurs when the substrate concentration is high), the enzyme concentration can be determined by measuring the rate of catalysis. Because many $k_{cat}$ values of β-lactamases with common β-lactam substrates are known, the concentration of a β-lactamase enzyme can be determined by measuring the rate of catalysis of a substrate at high substrate concentration (in units of product concentration formed per unit time). These types of measurements can be done using ECL.

For example, if one would like to quantitate the concentration of β-lactamase I from *Bacillus cereus* in a solution of defined pH, temperature and other factors, penicillin G could be added to give a sufficiently high concentration (such as 1.0 mM) so that the enzyme would operate at $V_{max}$. ECL measurements of penicillin turnover would be made at no fewer than two time points; for example at times=0, 1.0, 2.5, 5.0, 7.5, and 10.0 minutes after initiation of the enzyme-catalyzed reaction. By comparison of the ECL generated in a standard curve (concentration of hydrolyzed penicillin G vs. generated ECL), the initial rate of catalytic hydrolysis could be determined and this value would be the maximal velocity. Division of this experimentally-determined $V_{max}$ (for example, 2200 nM penicillin G hydrolyzed per second) by the literature-reported $k_{cat}$ value (for example, 2200 s$^{-1}$ (established in Martin, M. T. & Waley, S. G., *Biochem. J.* (1988) 254, pp. 923–925.) would give the enzyme concentration (1 nM).

Example 5

ECL Detection and Quantitation of β-Lactam Antibiotics in Biological Fluids Such as Blood, Serum, Urine, or Throat Swabs Detection of antibiotics in biological materials could be readily carried out following removal of any cells that might be present that could interfere with the ECL process or measurement. Cell removal can be carried out by well-known means such as filtration or centrifugation. The remaining fluid can then be measured for antibiotic-facilitated ECL as described elsewhere in this document. Two samples will be measured for ECL; one sample will be the patient's treated fluid, the other sample will be the same patient's fluid but containing an added β-lactamase enzyme known to hydrolyze that antibiotic will be measured for ECL (ECL will be measured following a sufficient incubation time for the enzyme to completely hydrolyze any antibiotic that may be present). The difference in ECL between the untreated and enzyme-treated samples will be indicative of the presence of the antibiotic and the extent of ECL difference will indicate the concentration of that antibiotic. A standard curve can be generated by adding to the fluid of the patient known amounts of the antibiotic and measuring ECL before and after enzyme-catalyzed hydrolysis. The standard curve should be generated using the same patient's fluid to which known concentrations of antibiotic have been added because the fluid may have substances in it which affect the ECL process or measurement that are unique to that particular patient.

Example 6

ECL Detection and Quantitation of fLactam Antibiotics in Food Such as Milk or Meat Detection of antibiotics in liquid foods such as milk can be carried out either directly on the liquid or after treatment to remove components such as lipids and proteins or other non-antibiotic substances that may interfere with the ECL process or measurement. Such removal steps are common laboratory procedures and may include high speed centrifugation (for example, 10,000 rpm in a standard laboratory centrifuge for 30 minutes). Centrifugation would cause a layer of solid fat to form on the surface of liquids such as milk. The layer of fat could be manually removed by using, for example, a spatula. Protein could be removed either by precipitation using ammonium sulfate or, preferably, by ultrafiltration. Ultrafiltration is a process of removing high molecular weight substances from liquids by pressurized filtration through a membrane containing defined nominal pore sizes (see Amicon catalog (Danvers, MA)) for ultrafiltration equipment and further information). In the case of antibiotics (which typically have molecular weights of less than 1000 Da), a membrane with a molecular weight cut-off of 10,000 Da might be best. Such membranes retain molecules with nominal molecular weight higher than 10,000 such that the filtrate would contain only low molecular weight (<10,000 Da) substances, including antibiotics. Higher molecular weight cut-off membranes (50,000–100,000 Da) might filter faster but would not retain as much potential ECL-interfering material.

Following any necessary treatments such as centrifugation and ultrafiltration, a defined volume of the liquid will then be measured for ECL by standard procedures described elsewhere in this document. An identical sample could be treated with a β-lactamase known to efficiently hydrolyze the β-lactam antibiotic suspected to be present in the liquid. Following sufficient time for hydrolysis (dependent on temperature, pH, and enzyme concentration) the second sample is measured for ECL. Since β-lactamases specifically hydrolyze β-lactam antibiotics but give little, or no ECL at the low concentrations (typically nanomolar) required for catalysis, the difference in ECL between the hydrolyzed and non-hydrolyzed samples will be an indication of the β-lactam antibiotic concentration in the liquid. To quantitate the concentration of detected antibiotic, a standard curve could be generated using known amounts of the antibiotic suspected to be present (hydrolyzed and unhydrolyzed). In generating a standard curve, it is preferable to add the known antibiotic to the food such as milk and treat the liquid the same as the unknown solutions (for example, by centrifugation and ultrafiltration). Testing of the analyzed material for different antibiotics could be done by repeating this experiment on similar samples but using different β-lactamases which would each specifically hydrolyze different antibiotics. Such repetitive treatment with different enzymes could help to identify the antibiotics that are present in the liquid.

Detection of antibiotics in solid food such as meat could be carried out similarly except that the antibiotic would have to be extracted (solubilized) from the solid food. Initially, a sample of the food could be suspended in buffer (preferably 0.1 M phosphate, pH 7.0) and minced in a blender until smooth. The antibiotic may be further extracted by sonication on ice which would disrupt any cells present, releasing any antibiotic present inside the cells. Following mincing and sonication, the material could be treated similarly to liquid food as described above. Namely, the material could be centrifuged and/or ultrafiltered. In the case of meat, centrifugation would primarily result in a pellet consisting of cellular debris (as opposed to milk in which centrifugation results in a surface fat layer). In generating standard curves, the known antibiotic should be added early in the process, preferably to the buffer used in mincing.

Beta-lactam antibiotics were detected in milk (Vitamin D Mil, Embassy Dairy, Waldorf, Md., Grade A pasteurized and homogenized). The following results were obtained for benzylpenicillin (300 μL total volume containing 250 μL milk, 10.0 μM Ru(bpy)$_3^{2+}$, 1.0 mM penicillin G, +/−18 nm β-lactamase I from *B. cereus*) and for cephalosporin C (300 μL total volume containing 250 μL milk, 10.0 μM Ru(bpy)$_3^{2+}$, 1.0 mM cephalosporin C, +/−18 nM β-lactamase P99 from *E. cloacae*).

| Sample | ECL Counts |
|---|---|
| Benzylpenicillin | |
| Milk + Ru(bpy)$_3^{2+}$ + penicillin | 1880 |
| Milk + Ru(bpy)$_3^{2+}$ + penicillin + enzyme | 10,100 |
| Cephalosporin C | |
| Milk + Ru(bpy)$_3^{2+}$ + cephalosporin C | 7960 |
| Milk + Ru(bpy)$_3^{2+}$ + ceph. C + enzyme | 9340 |

Similar experiments were carried out with antibiotics in milk hydrolyzed with NaOH;

| Sample | ECL Counts |
|---|---|
| Benzylpenicillin | |
| Milk + Ru(bpy)$_3^{2+}$ + penicillin | 19,100 |
| Milk + Ru(bpy)$_3^{2+}$ + Penicillin + NaOH | 64,400 |
| Cephalosporin | |
| Milk + Ru(byp)$_3^{2+}$ + cephalosporin C | 41,200 |
| Milk + Ru(bpy)$_3^{2+}$ + Ceph. C + NaOH | 35,100 |

As can be seen in the above tables for cephalosporin C, the effect of hydrolysis on the ECL depends on the method of hydrolysis; enzyme hydrolysis causes the counts to increase while NaOH hydrolysis causes the counts to decrease. Appropriate control experiments showed that this is not a result of the presence of enzyme. As described elsewhere in this document, NaOH hydrolysis of this compound is unusually method dependent, a phenomenon suspected to result from the formation of alternative ECL-active hydrolysis products. The results are reproducibly consistent within any given method of hydrolysis. Other experiments with centrifugation of the milk to remove fat gave similar results for both benzylpenicillin and cephalosporin C. Standard curves showed that less than 25 μM benzylpenicillin and less than 250 μM cephalosporin C could be detected in milk using ECL.

Example 7

ECL Assay of β-Lactamases in Biological Materials Such as Blood, Urine, Serum or Throat Swabs The determination of β-lactamases in biological materials would be carried out in a method similar to that described in Example 4. In essence, a known antibiotic would be mixed with the biological fluid to a known concentration (for example 1.0 mM). An immediate ECL reading could be made and another reading could be made at some time later (it could be 5 minutes if the concentration of β-lactamase is relatively high or as long as overnight if the β-lactamase concentration is low). A change in ECL would indicate antibiotic hydrolysis by a β-lactamase. The extent of antibiotic turnover could be compared to a standard curve of antibiotic concentration hydrolyzed vs. ECL generated. As with measurement of antibiotics in biological fluids as described in Example 5, it may be advisable to treat the fluid by known means to remove any non-β-lactamase substances that may interfere with the ECL process or measurement. The enzyme present in a throat swab may need to be solubilized by addition of buffer.

Example 8

ECL Assay of β-Lactamases in Food Such as Milk and Meat

Detection and quantitation of β-lactamases in liquid (such as milk) or solid (such as meat) foods can be carried out using ECL. In the case of liquid foods, appropriate known methods may be required to remove non-β-lactamase substances that may interfere with the ECL process or measurement. For example, filtration through common filter paper may be useful in removing particulates from milk. Also, centrifugation of milk would remove lipids which might interfere with measurements. In the case of solid foods such as meat, homogenization in a Waring #blender with added buffer (for example, 0.1 M phosphate, pH 7.0) followed by sonication at 4° C. and centrifugation (10,000×g for 30 minutes) would aid in enzyme solubilization. Following these procedures, it might also be useful to add an ultrafiltration step to remove molecules of over 100,000 Da. The ultrafiltration filtrate will contain any β-lactamases which generally have molecular weights of about 30,000 Da. The ECL detection of β-lactamases in these food-derived solutions would consist of first adding a chosen β-lactam antibiotic (for example, penicillin G to a concentration of 1.0 mM) and making an immediate ECL measurement followed by at least one more measurement some later time) (the times could be as short as 5 minutes or as long as overnight). Any change in ECL with would indicate the presence of β-lactamase-catalyed hydrolysis of the added antibiotic. The extent of hydrolysis could be determined by comparison with a standard curve (antibiotic concentration hydrolyzed vs. ECL) that has been generated under comparable conditions.

Example 9

ECL Assay of β-Lactamases in Bacterial Culture

It is preferable and sometimes essential to detect β-lactamases in a bacterial culture medium (such as in defined laboratory media or in blood, urine, or milk) without extensive isolation steps. In one application, in situ detection of β-lactamases in the blood of a patient infected with a pathogenic microbe could beneficially affect decisions regarding the medical treatment of that individual. In such an application, it may be prohibitively time-consuming or otherwise impractical to purify the β-lactamase in order to detect it. Thus, it is important to be able to detect β-lactamases in the presence of the microbe that produced it and in the culture medium in which the bacterium has grown.

Beta-lactamases are produced by both gram negative and gram positive bacteria. In the case of gram negative bacteria (e.g., *E. coli*), β-lactamases are sequestered in the periplasmic space. In gram positive bacteria (e.g., *B. cereus*), the enzyme is secreted into the medium surrounding the cell. It is valuable to be able to detect β-lactamase activity in both gram negative and gram positive bacterial cultures. Because the enzymes are present in physically different states (sequestered vs. secreted) in the two types of bacteria, β-lactamase detection may or may not require somewhat different experimental protocols.

Two strains of the gram negative bacterium, E. coli, were grown overnight at 30° C., each in 10 mL of LB culture medium. One strain, is called E. coli AmpR (ATCC: DH5βF'IQpDsubE.F4) because it is resistant to ampicillin due to production of β-lactamases. The other strain, termed E. coli AmpS(ATCC;Jm105), does not produce high levels of β-lactamase and was used as a control (ampicillin-sensitive) strain. The cells were isolated from the culture medium as a centrifugation pellet by centrifugation at 2800 rpm in a Sorvall RT 6000D centrifuge followed by removal of the supernatant solution by decanting. Tests were conducted with the decanted supernatant but, at least with E. coli, much more β-lactamase activity was detected in the pellet. The pelleted cells were resuspended in 9.5 μL of 50 mM Tris-acetate buffer, pH 8.0, then sonicated for 15 minutes in an ice-chilled beaker. Typically, portions of the resulting suspension (9.5–10.0, μL) were added to 300 μL of 0.1 M phosphate buffer, pH 7.5 containing 500 μM ampicillin, 10.0 μM Ru(bpy)$_3^{+2}$, and 0.05% Triton X-100. After various incubation times (none—overnight), the suspensions were tested for their ability to generate electrochemiluminescence using an IGEN ECL Analyzer. In some cases, 5.0 μL of a 1.0 mM solution of the β-lactamase inhibitor, 6-β-Br-penicillanic acid, was added as a control of the source of generated ECL.

A similar protocol was used with the gram negative bacterium, B. cereus. One strain secretes a relatively high amount of β-lactamase (termed B. cereus AmpR) (ATCC; 27348) and the other strain secretes little β-lactamase (termed B. cereus AmpR) (ATCC; 9139). The growth conditions and experimental procedures were identical as described above for E. coli except that in some cases, as will be described below, the supernatant solution was used for the ECL experiments.

The results for E. coli showed that β-lactamase activity associated with cell cultures could indeed be measured by using ECL without extensive purification. After a 1.0-hour incubation of E. coli samples with 500 μM ampicillin solutions, the following ECL results were obtained:

TABLE 3

ECL Detection of β-Lactamase Activity in E. coli

| Sample | ECL Counts |
| --- | --- |
| E. coli AmpS + Ru(bpy)$_3^{2+}$ + ampicillin | 36,400 |
| E. coli AmpR + Ru(bpy)$_3^{2+}$ + ampicillin | 106,000 |
| E. coli AmpS + Ru(bpy)$_3^{2+}$ + 6-β-Br-penicillanic acid + ampicillin | 35,000 |
| E. coli AmpR + Ru(bpy)$_3^{2+}$ 6-,B-Br-penicillanic acid + ampicillin | 36,700 |

These data demonstrate that β-lactamase activity can be detected in situ in gram negative bacteria. Similar results were obtained with the gram positive bacterium B. cereus, but using the centrifugation supernatant rather than the pellet. Once again the results were obtained after a 1.0-hour incubation with 500 μM ampicillin.

TABLE 4

ECL Detection of β-Lactamase Activity in B. cereus

| Sample | ECL Counts |
| --- | --- |
| B. cereus AmpS + Ru(bpy)$_3^{2+}$ + ampicillin | 33,600 |
| B. cereus AmpR + Ru(bpy)$_3^{2+}$ + ampicillin | 47,200 |
| B. cereus AmpS + Ru(bpy)$_3^{2+}$ + 6-β-Br-penicillanic acid + ampicillin | 25,600 |

TABLE 4-continued

ECL Detection of β-Lactamase Activity in B. cereus

| Sample | ECL Counts |
| --- | --- |
| B. cereus AmpR + Ru(bpy)$_3^{2+}$ + 6-β-Br-penicillanic acid + ampicillin | 22,500 |

These results demonstrate that β-lactamase secreted by gram positive cells can be detected in one hour by ECL.

Figure 22:
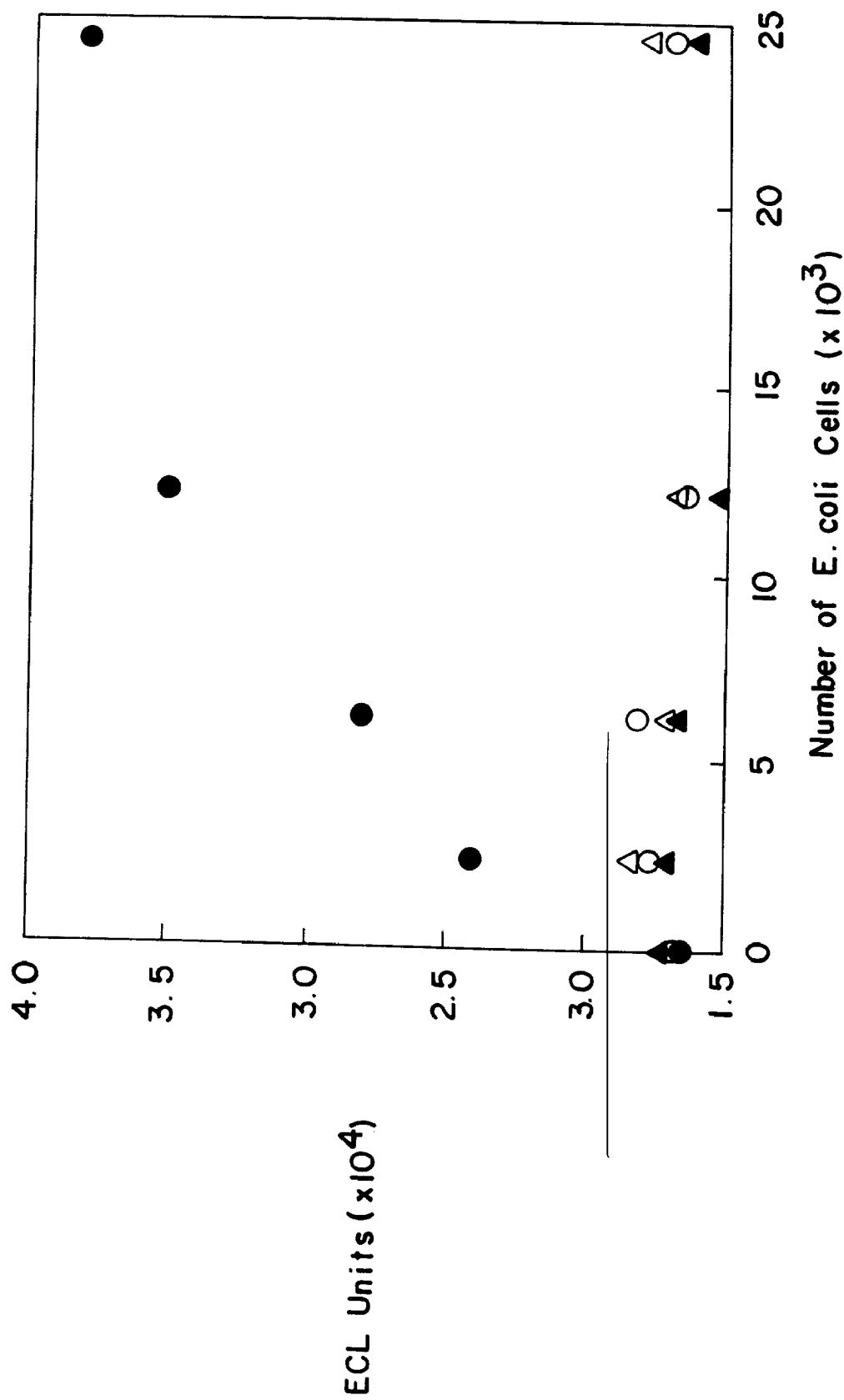
FIG. 22 shows quantitation of bacterial cells by ECL measurement of their β-lactamase activity. Various amounts of *E. coli* extract (centrifugation pellet) were incubated overnight in 1.0 mM ampicillin. In some cases, the β-lactamase inhibitor 6-β-Br-penicillanic acid was also added. Incubated mixtures consisted of 1.0 mM ampicillin and 0.1 M sodium phosphate, pH 7.5 and either AmpS *E. coli* (low levels of β-lactamase)(open triangles), AmpS *E. coli* plus 6-β-Br-penicillanic acid (closed triangles), AmpR *E. coli* (high levels of β-lactamase) (closed circles), or AmpR *E. coli* plus 6-β-Br-penicillanic acid (open circles). To aliquots of the overnight-incubated samples was added Ru(bpy)$_3^{2+}$ and Triton X-100 to give final concentrations of 10 ILM and 0.05%, respectively. ECL was measured using an IGEN ECL instrument.
Figure 23:
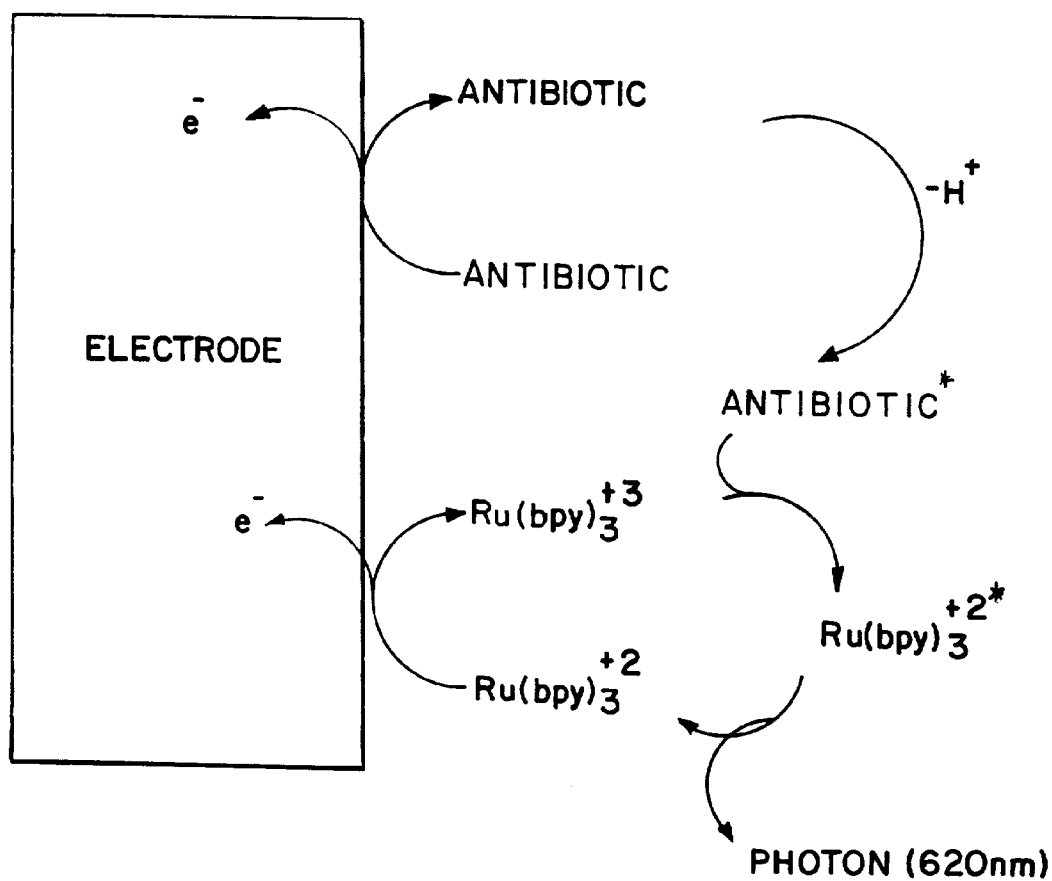
FIG. 23 illustrates a possible ECL reaction mechanism for antibiotics. In some cases, the hydrolysis product participates in this reaction to elicit light. However, in all cases tested, there is a substantial difference between a given antibiotic and its hydrolysis product.

In some applications, rapid detection of β-lactamases may not be as critical as the detection of a small number of bacterial cells that may be present in a sample. Experiments were carried out to determine the lowest number of cells detectable by their β-lactamase activity under the conditions used. Using cultures of E. coli grown overnight in standard (LB) growth media, increasingly greater dilutions of culture centrifugation pellets were tested by overnight incubations with ampicillin in a similar methodology as described above. E. coli concentrations in cell culture were determined by spectrophotometric absorbance at 600 μm and subsequent comparison to absorbances of plated cultures. As seen in FIG. 22, the lower detection limit of E. coli cells in an overnight incubation was 2440.

Example 10

Identification of Bacteria by ECL Assay of Their Beta-Lactamases

There are many different types of β-lactamase enzymes. The structures (amino acid sequences) can differ substantially between enzymes as well as their substrate specificities. Because there are many different β-lactam antibiotics and many different β-lactamases, almost all β-lactamases can in theory be identified by the relative extent of hydrolysis of a series of different β-lactam antibiotic substrates (that is by its individual "spectrum" of substrate specificity). A given bacterial strain could be identified by its unique β-lactamase substrate specificity (see FIGS. 20a–d). In identifying a given unknown bacterial strain, appropriately-treated aliquots of that strain (pellet or supernatant as described in Example 9) could be mixed with a series of appropriately diverse antibiotics (including both cephalosporins and penicillins). After an appropriate length of time (from 5 minutes to overnight), the ECL of the different incubation mixtures could be read and compared with appropriate standards to determine relative rates of turnover of the different antibiotics from 0–100% turnover is expected depending on the enzyme concentration and the individual antibiotic/enzyme pair). Based on known substrate specificities for known bacterial strains, the bacterial species in question could be identified.

Although the examples illustrate various modifications of the present invention, other variations will suggest themselves to those skilled in the art in light of the above disclosure. It is to be understood, therefore, that changes may be made in the particular embodiments described above which are within the full intended scope of the inventions as defined in the appended claims.

We claim:

1. A method of electrochemiluminescently determining an analyte of interest in a sample, which comprises exposing a sample to a combination of an electrochemiluminescent label containing a coordinate complex of a metal, said label being linked to an electrochemiluminescence coreactant species in an amount indicative of the presence or amount of the analyte of interest, to conditions suitable for inducing electrochemiluminescence, and determining emitted luminescence.

2. A compound for determining an analyte of interest in a sample, which comprises an electrochemiluminescent label containing a coordinate complex of a metal, which label is linked to an electrochemiluminescence coreactant species in an amount indicative of the presence or amount of the analyte of interest, such that said compound electrochemiluminesces when exposed to electrochemical energy.

3. A compound for determining an analyte of interest in a sample, which comprises an electrochemiluminescent label containing a coordinate complex of a metal, which label is linked to a catalyst substrate wherein the catalyst substrate and corresponding catalytic product differ in ability to act as electrochemiluminescence coreactants for said electrochemiluminescent label.

4. A system for electrochemiluminescently determining an analyte of interest in a sample, which comprises
   (a) a compound which comprises an electrochemiluminescent label containing a coordinate complex of a metal, which label is linked to an electrochemiluminescence coreactant species in an amount indicative of the presence or amount of the analyte of interest;
   (b) means for exposing said compound to electrochemical energy; and
   (c) means for detecting emitted luminescence.

5. The method of claim 1, wherein said species and the product of said catalytic reaction derived from said species differ in ability to act as electrochemiluminescence coreactants for said electrochemiluminescent label.

6. The compound of claim 2, wherein said species and the product of said catalytic reaction derived from said species differ in ability to act as electrochemiluminescence coreactants for said electrochemiluminescent label.

7. The system of claim 4, wherein said species and the product of said catalytic reaction derived from said species differ in ability to act as electrochemiluminescence coreactants for said electrochemiluminescent label.

8. The method of claim 1, wherein the electrochemiluminescent coreactant species is a species capable of interacting with said electrochemiluminescent label to induce said label to electrochemiluminesce.

9. The compound of claim 2, wherein the electrochemiluminescent coreactant species is a species capable of interacting with said electrochemiluminescent label to induce said label to electrochemiluminesce.

* * * * *